United States Patent
Miao et al.

(10) Patent No.: US 10,464,985 B2
(45) Date of Patent: *Nov. 5, 2019

(54) COMPOUNDS WITH REDUCED RING SIZE FOR USE IN DIAGNOSING AND TREATING MELANOMA, INCLUDING METASTATIC MELANOMA AND METHODS RELATED TO SAME

(71) Applicant: STC.UNM, Albuquerque, NM (US)

(72) Inventors: Yubin Miao, Albuquerque, NM (US); Haixun Guo, Louisville, KY (US)

(73) Assignee: STC.UNM, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/039,858

(22) Filed: Jul. 19, 2018

(65) Prior Publication Data
US 2019/0106474 A1     Apr. 11, 2019

Related U.S. Application Data

(63) Continuation of application No. 14/622,217, filed on Feb. 13, 2015, now Pat. No. 10,047,135, which is a continuation of application No. 13/497,738, filed as application No. PCT/US2010/058282 on Nov. 30, 2010, now Pat. No. 8,986,651.

(60) Provisional application No. 61/283,174, filed on Nov. 30, 2009.

(51) Int. Cl.
| | |
|---|---|
| A61K 51/00 | (2006.01) |
| A61M 36/14 | (2006.01) |
| C07K 14/68 | (2006.01) |
| A61K 51/08 | (2006.01) |
| A61K 45/06 | (2006.01) |
| C07K 7/54 | (2006.01) |
| A61K 38/00 | (2006.01) |

(52) U.S. Cl.
CPC .............. *C07K 14/68* (2013.01); *A61K 45/06* (2013.01); *A61K 51/08* (2013.01); *A61K 51/086* (2013.01); *A61K 51/088* (2013.01); *C07K 7/54* (2013.01); *A61K 38/00* (2013.01)

(58) Field of Classification Search
CPC ........ C07K 14/68; C07K 7/54; A61K 51/088; A61K 51/086; A61K 45/06; A61K 51/08; A61K 38/00
USPC ...................................................... 424/1.69
See application file for complete search history.

(56) References Cited

U.S. PATENT DOCUMENTS

| | | |
|---|---|---|
| 6,607,709 B1 | 8/2003 | Jurisson |
| 8,603,435 B2 | 12/2013 | Miao |
| 2001/0038822 A1 | 11/2001 | Jurisson et al. |
| 2002/0054855 A1 | 5/2002 | Hoffman et al. |
| 2004/0254339 A1 | 12/2004 | Saviano |
| 2007/0269375 A1 | 11/2007 | Chen et al. |

FOREIGN PATENT DOCUMENTS

WO     2009089066 A2     7/2009

OTHER PUBLICATIONS

Miao Y, et al. 111In-Labeled Lactam Bridge-Cyclized alpha-Melanocyte Stimulating Hormone Peptide Analogues for Melanoma Imaging. Bioconjugate Chem, 2008;19:539-547.

Shi J, et al. Improving Tumor Uptake and Excretion Kinetics of 99mTc-Labeled Cyclic Arginine-Glycine-Aspartic (RGD) Dimers with Triglycine Linkers. J Med Chem, 2008;51:7980-7990.

Guo H, et al. Effects of the Amino Acid Linkers on the Melanoma-Targeting and Pharmacokinetic Properties of 111In-Labeled Lactam Bridge-Cyclized alpha-MSH Peptides. The Journal of Nuclear Medicine, 2011;52(4):608-616.

Jemal A, Siegel R, Ward E, Hao Y, Xu J, Thun MJ. Cancer statistics, 2009. CA Cancer J Clin. 2009;59:225-249.

Alonso O, Martinez M, Delgado L, et al. Staging of regional lymph nodes in melanoma patients by means of 99mTc-MIBI scintigraphy. J Nucl Med. 2003;44:1561-1565.

Nabi HA, Zubeldia JM. Clinical application of 18F-FDG in oncology. J Nucl Med Technol. 2002;30:3-9.

Dimitrakopoulou-Strauss A, Strauss LG, Burger C. Quantitative PET studies in pretreated melanoma patients: A comparison of 6-[18F]fluoro-L-DOPA with 18F-FDG and 15O-water using compartment and non-compartment analysis. J Nucl Med. 2001;42:248-256.

(Continued)

*Primary Examiner* — Michael G. Hartley
*Assistant Examiner* — Sean R Donohue
(74) *Attorney, Agent, or Firm* — Henry D. Coleman; R. Neil Sudol

(57) ABSTRACT

The present invention is directed to novel non-invasive diagnostic tools/compounds to image cancers, especially, melanoma, including metastatic melanoma in vivo. The present compounds exhibit enhanced uptake in cancerous cells and tissue and decreased renal uptake in kidney, evidencing favorable pharmacokinetics of compounds of the present invention. The compounds according to the present invention represent an advance in the diagnosis and treatment of melanoma, including metastatic melanoma using non-invasive molecular imaging techniques. The novel probes of the present invention are also useful for initiating therapy for melanoma as well as monitor patients' response to chemotherapy treatments and other interventions or therapies used in the treatment of melanoma/metastatic melanoma. Compounds according to the present invention may be used as diagnostic tools for a number of conditions and diseases states as well as therapeutic agents for treating such conditions and disease states.

29 Claims, 12 Drawing Sheets

(56) References Cited

OTHER PUBLICATIONS

Miao Y, Whitener D, Feng W, Owen NK, Chen J, Quinn TP. Evaluation of the human melanoma targeting properties of radiolabeled alpha-melanocyte stimulating hormone peptide analogues. Bioconjug Chem. 2003;14:1177-1184.

Miao Y, Owen NK, Whitener D, Gallazzi F, Hoffman TJ, Quinn TP. In vivo evaluation of 188Re-labeled alpha-melanocyte stimulating hormone peptide analogs for melanoma therapy. Int J Cancer. 2002;101:480-487.

Chen J, Cheng Z, Hoffman TJ, Jurisson SS, Quinn TP. Melanoma-targeting properties of 99mtechnetium-labeled cyclic alpha-melanocyte-stimulating hormone peptide analogues. Cancer Res. 2000;60:5649-5658.

Siegrist W, Solca F, Stutz S, et al. Characterization of receptors for alpha-melanocyte-stimulating hormone on human melanoma cells. Cancer Res. 1989;49:6352-6358.

Tatro JB, Reichlin S. Specific receptors for alpha-melanocyte-stimulating hormone are widely distributed in tissues of rodents. Endocrinology 1987;121:1900-1907.

Miao Y, Owen NK, Fisher DR, Hoffman TJ, Quinn TP. Therapeutic efficacy of a 188Re-labeled alpha-melanocyte-stimulating hormone peptide analog in murine and human melanoma-bearing mouse models. J Nucl Med. 2005;46:121-129.

Miao Y, Hylarides M, Fisher DR, et al. Melanoma therapy via peptide-targeted alpha-radiation. Clin Cancer Res. 2005;11:5616-5621.

Froidevaux S, Calame-Christe M, Tanner H, Eberle AN. Melanoma targeting with DOTA-alpha-melanocyte-stimulating hormone analogs: structural parameters affecting tumor uptake and kidney uptake. J Nucl Med. 2005;46:887-895.

Froidevaux S, Calame-Christe M, Schuhmacher J, et al. A gallium-labeled DOTA-alpha-melanocyte-stimulating hormone analog for PET imaging of melanoma metastases. J Nucl Med. 2004;45:116-123.

Froidevaux S, Calame-Christe M, Tanner H, Sumanovski L, Eberle AN. A novel DOTA-alpha-melanocyte-stimulating hormone analog for metastatic melanoma diagnosis. J Nucl Med. 2002;43:1699-1706.

Wei L, Butcher C, Miao Y, et al. Synthesis and biologic evaluation of 64Cu-labeled rhenium-cyclized alpha-MSH peptide analog using a cross-bridged cyclam chelator. J Nucl Med. 2007;48:64-72.

Miao Y, Benwell K, Quinn TP. 99mTc- and 111In-labeled alpha-melanocyte-stimulating hormone peptides as imaging probes for primary and pulmonary metastatic melanoma detection. J Nucl Med. 2007;48:73-80.

Cheng Z, Chen J, Miao Y, Owen NK, Quinn TP, Jurisson SS. Modification of the structure of a metallopeptide: synthesis and biological evaluation of 111In-labeled DOTA-conjugated rhenium-cyclized alpha-MSH analogues. J Med Chem. 2002;45:3048-3056.

Cheng Z, Xiong Z, Subbarayan M, Chen X, Gambhir SS. 64Cu-labeled alpha-melanocyte-stimulating hormone analog for MicroPET imaging of melanocortin 1 receptor expression. Bioconjug Chem. 2007;18:765-772.

Miao Y, Gallazzi F, Guo H, Quinn TP. 111In-labeled lactam bridge-cyclized alpha-melanocyte stimulating hormone peptide analogues for melanoma imaging. Bioconjug Chem. 2008;19:539-547.

Guo H, Shenoy N, Gershman BM, Yang J, Sklar LA, Miao Y. Metastatic melanoma imaging with an 111In-labeled lactam bridge-cyclized alpha-melanocyte-stimulating hormone peptide. Nucl Med Biol. 2009;36:267-276.

Sawyer TK, Hruby VJ, Darman PS, Hadley ME. [half-Cys4,half-Cys10]-a-melanocyte-stimulating hormone: a cyclic a-melanotropin exhibiting superagonist biological activity. Proc Natl Acad Sci USA. 1982;79:1751-1755.

Al-Obeidi F, Hadley ME, Pettitt BM, Hruby VJ. Design of a new class of superpotent cyclic a-melanotropins based on quenched dynamic simulations. J Am Chem Soc. 1989;111:3413-3416.

Al-Obeidi F, de L Castrucci AM, Hadley ME, Hruby VJ. Potent and prolonged-acting cyclic lactam analogs of α-melanotropin: design based on molecular dynamics. J Med Chem. 1989;32:2555-2561.

Fung S, Hruby VJ. Design of cyclic and other templates for potent and selective peptide a-MSH analogues. Curr Opin Chem Biol. 2005:9:352-358.

Haskell-Luevano C, Miwa H, Dickinson C, et al. Characterizations of the unusual dissociation properties of melanotropin peptides from the melanocortin receptor, hMC1R. J Med Chem. 1996;39:432-435.

Haskell-Luevano C, Toth K, Boteju L, et al. Beta-Methylation of the Phe7 and Trp9 melanotropin side chain pharmacophores affects ligand-receptor interactions and prolonged biological activity. J Med Chem. 1997;40:2740-2749.

Chen J, Cheng Z, Owen NK, et al. Evaluation of an 111In-DOTA-rhenium cyclized alpha-MSH analog: a novel cyclic-peptide analog with improved tumor-targeting properties. J Nucl Med. 2001;42:1847-1855.

Raposinho PD, Xavier C, Correia JD, Falcao S, Gomes P, Santos I. Melanoma targeting with alpha-melanocyte stimulating hormone analogs labeled with fac-[99mTc(CO)3]+: effect of cyclization on tumor-seeking properties. J Biol Inorg Chem. 2008;13:449-459.

Raposinho PD, Correia JD, Alves S, Botelho MF, Santos AC, and Santos I. A 99mTc(CO)3-labeled pyrazolyl—α-melanocyte-stimulating hormone analog conjugate for melanoma targeting. Nucl Med Biol. 2008;35:91-99.

Guo H, Yang J, Gallazzi F, Prossnitz ER, Sklar LA, Miao Y. Effect of DOTA position on melanoma targeting and pharmacokinetic properties of 111In-labeled lactam bridge-cyclized α-melanocyte stimulating hormone peptide. Bioconjug Chem 2009;20:2162-68.

Guo H, Yang J, Shenoy N, Miao Y. Gallium-67-labeled lactam bridge-cyclized alpha-melanocyte stimulating hormone peptide for primary and metastatic melanoma imaging. Bioconjug Chem 2009;20:2356-63.

Guo H, Yang J, Gallazzi F, Miao Y. Reduction of the ring size of radiolabeled lactam bridge-cyclized alpha-MSH peptide resulting in enhanced melanoma uptake. J Nucl Med 2010;51:418-26.

Hoffman TJ, Gali H, Smith CJ, Sieckman GL, Hayes DL, Owen NK, Volkert WA. Novel series of 111In-labeled bombesin analogs as potential radiopharmaceuticals for specific targeting of gastrin-releasing peptide receptors expressed on human prostate cancer cells. J Nucl Med 2003; 44:823-31.

Garayoa EG, Schweinsberg C, Maes V, Brans L, Blauenstein P, Tourwe DA, Schibli R, Schbiger PA. Influence of the molecular charge on the biodistribution of bombesin analogues labeled with the [99mTc(CO)3]-core. Bioconjug Chem 2008;19:2409-16.

Fragogeorgi EA, Zikos C, Gourni E, Bouziotis P, Paravatou-Petsotas M, Loudos G, Mitsokapas N, Xanthopoulos S, Mavri-Vavayanni M, Livaniou E, Varvarigou AD, Archimandritis SC. Spacer site modifications for the improvement of the in vitro and in vivo binding properties of 99mTc-N3S-X-Bombesin[2-14] derivatives. Bioconjug Chem 2009; 20: 856-67.

Garrison JC, Rold TL, Sieckman GL, Naz F, Sublett SV, Figueroa SD, Volkert WA, Hoffman TJ. Evaluation of the pharmacokinetic effects of various linking group using the 111In-DOTA-X-BBN(7-14)NH2 structural paradigm in a prostate cancer model. Bioconjug Chem 2008; 19: 1803-12.

Parry JJ, Kelly TS, Andrews R, Rogers BE. In vitro and in vivo evaluation of 64Cu-labeled DOTA-Linker-Bombesin (7-14) analogues containing different amino acid linker moieties. Bioconjug Chem 2007;18:1110-7.

Liu S, He Z, Hsieh WY, Kim YS, Jiang Y. Impact of PKM linkers on biodistribution charateristics of the 99mTc-labeled cyclic RGDfK dimer. Bioconjug Chem 2006;17:1499-507.

Shi J, Wang L, Kim YS, Zhai S, Liu Z, Chen X, Liu S. Improving tumor uptake and excretion kinetics of 99mTc-labeled cyclic arginine-glycine-aspartic (RGD) dimers with triglycine linkers. J Med Chem 2008;51:7980-90.

Wang L, Shi J, Kim YS, Zhai S, Jia B, Zhao H, Liu Z, Wang F, Chen X, Liu S. Improving tumor-targeting capability and pharmacokinetics of 99mTc-labeled cyclic RGD dimers with PEG4 linkers. Mol Pharm 2009;6:231-45.

(56) References Cited

OTHER PUBLICATIONS

Shi J, Kim YS, Zhai S, Liu Z, Chen X, Liu S. Improving tumor uptake and pharmacokinetics of 64Cu-labeled cyclic RGD peptide dimers with Gly3 and PEG4 linkers. Bioconjug Chem 2009;20:750-9.

Schweinsberg C. Novel 99mTc-labeled Bombesin Analogues with Improved Pharmacokinetics for Targeting of Gastrin-releasing-Peptide Receptor-Positive Tumors; PhD Dissertation, Swiss Federal Institute of Technology Zurich 2008; DISS. ETH No. 17952.

Clarke, et al. Inorganica Chimica Acta, 1991;181:273-280.

A: DOTA-GlyGlu-CycMSH

B: DOTA-Re(Arg¹¹)CCMSH

C: DOTA-Nle-CycMSH_hex

DOTA-Nle-CycMSH$_{hex}$

| Linker | Peptide abbreviation |
|---|---|
| X= Nle | DOTA-Nle-CycMSH$_{hex}$ |
| X= GlyGlyNle | DOTA-GGNle-CycMSH$_{hex}$ |
| X= GlyGluNle | DOTA-GENle-CycMSH$_{hex}$ |
| X= NleGlyGlu | DOTA-NleGE-CycMSH$_{hex}$ |

Hynic-Linker-Nle-CycMSH$_{hex}$

DOTA-Linker-Nle-CycMSH$_{hex}$

COMPOUNDS WITH REDUCED RING SIZE FOR USE IN DIAGNOSING AND TREATING MELANOMA, INCLUDING METASTATIC MELANOMA AND METHODS RELATED TO SAME

This application is a continuation application of U.S. patent application Ser. No. 14/622,217 filed Feb. 13, 2015, which is a continuation application of U.S. national phase patent application Ser. No. 13/497,738 filed Apr. 9, 2012 which is a 371 application of international patent application number PCT/US2010/058282 filed in the United States Receiving Office on Nov. 30, 2010 which claims the benefit of priority of U.S. provisional application Ser. No. 61/283,174, filed Nov. 30, 2009, all of which priority applications are incorporated by reference in their entirety herein.

RELATED APPLICATIONS AND GOVERNMENT SUPPORT

The present invention was made with Government support under grant no. DOD grant W81XWH-09-1-0105 and NIH grant NM-INBRE P20RR016480 from the United States DOD/NIH. Consequently, the U.S. government has certain rights in the invention.

FIELD OF THE INVENTION

The present invention is directed to novel non-invasive diagnostic tools/compounds to image cancers, especially, melanoma, including metastatic melanoma in vivo. The present compounds exhibit enhanced uptake in cancerous cells and tissue and decreased renal uptake in kidney, suggesting favorable pharmacokinetics of compounds of the present invention. The compounds according to the present invention represent an advance in the diagnosis and treatment of melanoma, including metastatic melanoma using non-invasive molecular imaging techniques. The novel probes of the present invention will also be useful to initiate therapy for melanoma as well as monitor patients response to chemotherapy treatments and other interventions or therapies used in the treatment of melanoma/metastatic melanoma. Compounds according to the present invention may be used as diagnostic tools for a number of conditions and diseases states as well as therapeutic agents for treating such conditions and disease states.

BACKGROUND OF THE INVENTION

Skin cancer is the most commonly diagnosed cancer in the United States. Melanoma accounts for less than 5% of skin cancer cases but causes greater than 75% deaths of skin cancer. It was predicted that 68,720 new cases would be diagnosed and 8,650 deaths would occur in 2009 (1). Early diagnosis and prompt surgical removal are a patient's best opportunity for a cure since no curative treatment exists for metastatic melanoma. Despite the clinical use of 2-[$^{18}$F]fluoro-2-deoxy-D-glucose ([$^{18}$F]FDG) for positron emission tomography (PET) diagnosis and staging of melanoma, [$^{18}$F]FDG is not melanoma-specific imaging agent and is also not effective in imaging small melanoma metastases (<5 mm) and melanomas that have primary energy sources other than glucose (2-4). Alternatively, melanocortin-1 (MC1) receptor is a distinct molecular target due to its overexpression on both human and mouse melanoma cells (5-9). Radiolabeled α-melanocyte stimulating hormone (α-MSH) peptides can bind the MC1 receptors with nanomolar binding affinities (10-18) and represent a class of promising melanoma-specific radiopharmaceuticals for melanoma imaging and therapy.

Recently, the inventors have developed a novel class of $^{111}$In-labeled lactam bridge-cyclized DOTA-conjugated α-MSH peptides for melanoma detection (19, 20). Lactam bridge-cyclization was employed to improve the stabilities of the α-MSH peptides against the proteolytic degradations in vivo and enhance the binding affinities of the α-MSH peptides through stabilizing their secondary structures such as beta turns (21-24). The radiometal chelator DOTA was attached to the N-terminus of the lactam bridge-cyclized α-MSH peptide (12-amino acids in the peptide ring) for $^{111}$In radiolabeling. For instance, $^{111}$In-DOTA-GlyGlu-CycMSH (DOTA-Gly-Glu-c[Lys-Nle-Glu-His-DPhe-Arg-Trp-Gly-Arg-Pro-Val-Asp]) exhibited high MC1 receptor-mediated tumor uptake (10.40±1.40% ID/g at 2 h post-injection) in flank B16/F1 melanoma-bearing C57 mice (19). Both flank primary and pulmonary metastatic melanoma lesions were clearly visualized by small animal SPECT/CT using $^{111}$In-DOTA-GlyGlu-CycMSH as an imaging probe (19, 20), highlighting its potential as an effective imaging probe for melanoma detection.

One advantage of the lactam bridge-cyclized α-MSH peptide is that the peptide ring size can be finely modified by either adding or deleting amino acids without sacrificing the binding affinity of the peptide (19, 20). The studies on the α-MSH peptide agonists for the MC1 receptor revealed that the lactam bridge-cyclized α-MSH peptide with a 6-amino acid peptide ring {Ac-Nle-c[Asp-His-DPhe-Arg-Trp-Lys (CONH$_2$)], MT-II} displayed not only higher MC1 receptor binding affinity, but also slower MC1 receptor dissociation rate than the native α-MSH peptide {Ac-Ser-Tyr-Ser-Met-Glu-His-Phe-Arg-Trp-Gly-Lys-Pro-Val-NH$_2$} (25, 26). Slow MC1 receptor dissociation rate might contribute to the prolonged biological activity of MT-II in vitro and in vivo (25). In this study, we conjugated the radiometal chelator DOTA to the N-terminus of the MT-II peptide to generate a novel DOTA-conjugated lactam bridge-cyclized α-MSH peptide with a 6-amino acid peptide ring (DOTA-Nle-CycMSH$_{hex}$) to examine the effect of peptide ring size on its melanoma targeting and pharmacokinetic properties. The MC1 receptor binding affinity of DOTA-Nle-CycMSH$_{hex}$ was determined in B16/F1 melanoma cells. DOTA-Nle-CycMSH$_{hex}$ was radiolabeled with $^{111}$In which is a commercial available diagnostic radionuclide with a half-life of 2.8 days. The melanoma targeting and pharmacokinetic properties and SPECT/CT imaging of $^{111}$In-labeled DOTA-Nle-CycMSH$_{hex}$ were determined in B16/F1 melanoma-bearing C57 mice.

BRIEF DESCRIPTION OF THE INVENTION

Figure 1:
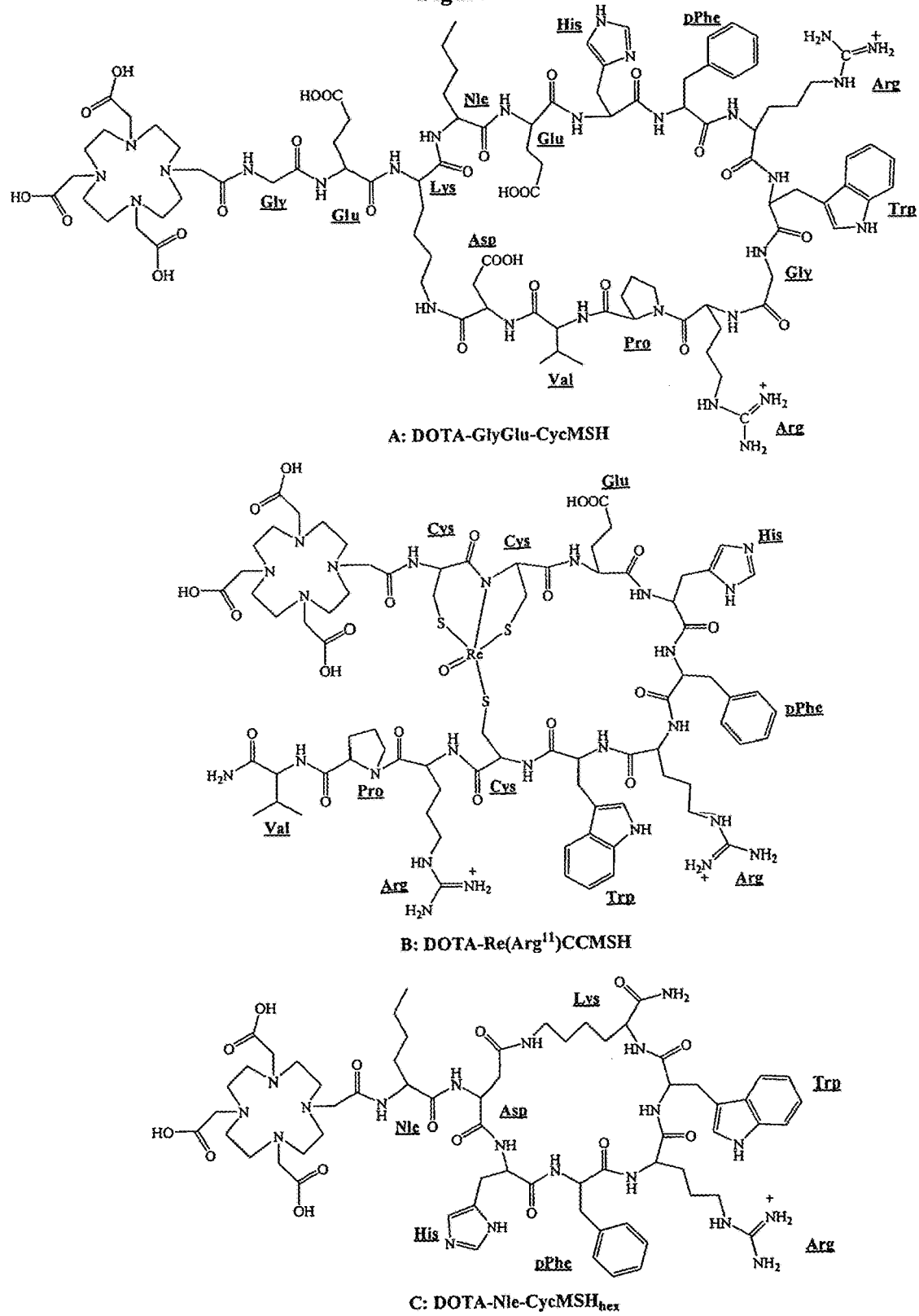
FIG. 1 shows the structures of DOTA-GlyGlu-CycMSH (A), DOTA-Re(Arg$^{11}$)CCMSH (B) and DOTA-Nle-CycMSH$_{hex}$ (C).

The present invention relates to compounds according to the general structure:

Where $Y^1$ is a chelate group, wherein $Y^1$ optionally incorporates or complexes with a radioisotope;
Each X is independently an amino acid residue (preferably, for example, a neutral amino acid such as norleucine (Nle), leucine or isoleucine, more preferably norleucine (Nle), or glycine or alanine, preferably glycine) which may be optionally acylated (preferably C$_2$-C$_{20}$ acylated) at its amino terminal end or an amino acid linker comprising an alkylene group or an ethylene glycol containing group according to the chemical structure:

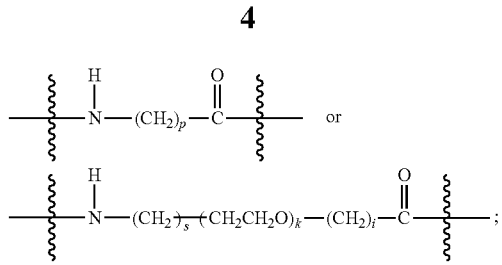

ABC is an amino acid linker wherein
A is absent or is a neutral or negatively charged amino acid at physiological pH which is optionally acylated at its amino terminal end;
B is a neutral or negatively charged amino acid at physiological pH which is optionally acylated (preferably C$_2$-C$_{20}$ acylated) at its amino terminal end;
C is absent or is a neutral or negatively charged amino acid at physiological pH;
m is an integer from 0 to 250, preferably 0 to 5, preferably 0 or 1;
n is 0 or 1, preferably 1;
p is an integer from 0 to 20, preferably 0 to 10;
k is an integer from 0 to 10, preferably 1 or 2;
Each i is an integer from 0 to 10, preferably 1 or 2;
Each s is an integer from 0 to 10, preferably 0, 1 or 2, preferably 0;
q is 0 or 1 (preferably 1), and
CycMSH$_{hex}$ is a cyclic peptide comprising six amino acids according to the general structure:

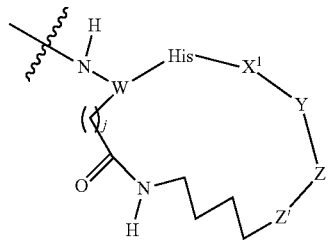

Wherein W is a C—H group from an aspartic acid or glutamic acid residue (preferably an aspartic acid residue), wherein the alkylene carboxylic acid sidechain of said aspartic acid or glutamic acid and the alkyleneamine sidechain of lysine are bonded together to form an amide linkage as indicated;
$X^1$ is phenylalanine, tyrosine or tryptophan, preferably D-phenylalanine;
Y is arginine or lysine, preferably arginine;
Z is tryptophan, phenylalanine or tyrosine, preferably tryptophan;
Z' is Lys(CONH$_2$) or Orn(CONH$_2$), preferably Lys(CONH$_2$);
j is 1 or 2 (preferably 1) or
a pharmaceutically acceptable salt thereof,
wherein said compound is optionally complexed with at least one radioisotope, preferably a polyvalent cationic radioisotope, even more preferably selected from the group consisting of $^{86}$Y $^{90}$Y, $^{111}$In, $^{177}$Lu, $^{225}$Ac, $^{212}$Bi, $^{213}$Bi, $^{66}$Ga, $^{67}$Ga, $^{68}$Ga, $^{64}$Cu, $^{67}$Cu, $^{71}$As, $^{72}$As, $^{76}$As, $^{77}$As, $^{65}$Zn, $^{48}$V, $^{203}$Pb, $^{209}$Pb, $^{212}$Pb, $^{166}$Ho, $^{149}$Pm, $^{153}$Sm, $^{201}$Tl, $^{188}$Re, $^{186}$Re and $^{99m}$Tc.

In preferred aspects of the invention, the compound incorporates or is complexed with a radioisotope as otherwise described herein. In certain aspects of the invention, $Y^1$ is a radical (i.e., linked to a linker or peptide as otherwise described herein) of DOTA (1,4,7,10-tetraazacyclododecane-1,4,7,10-tetraacetic acid), CB-TE2A (4,11-bis(carboxymethyl)-1,4,8,11-tetraazabicyclo[6.6.2]hexadecane), NOTA (1,4,7-triazacyclononane-1,4,7-triacetic acid), DTPA (Diethylenetriaminopentaacetic acid), $MAG_3$ (Mercaptoacetyltriglycine) and 4,5-bis(2-mercaptoacetamido)pentanoic acid and HYNIC (hydrazinonicotinamide). Other chelating moieties that can complex to radioisotopes are otherwise disclosed herein. In alternative preferred aspects of the invention, $CycMSH_{hex}$ is a cyclic peptide comprising six amino acids according to the general structure:

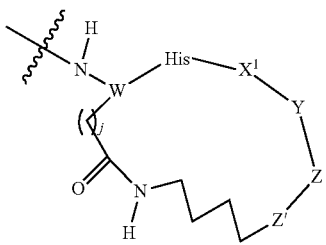

In preferred aspects of the invention, $Y^1$ is a DOTA radical according to the chemical structure:

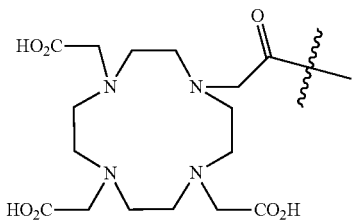 [SMILES: *C(=O)CN1CCN(CC(=O)O)CCN(CC(=O)O)CCN(CC(=O)O)CC1]

or a pharmaceutically acceptable salt thereof.

In additional preferred aspects of the above-described compounds, n is 0, or when n is 1, ABC may be a two or three amino acid unit linker (A or C may be absent) wherein one, and in certain instances, two or three (preferably, no more than two) of the amino acid units are negatively charged at physiological pH, e.g. aspartic or glutamic acid, preferably glutamic acid. In other aspects of the invention, ABC is a three amino acid unit linker wherein no more than one of the amino acid units is negatively charged at physiological pH and the other amino acid units are neutral at physiological pH. Preferably, the neutral amino acid is norleucine, leucine, glycine or alanine, preferably norleucine or glycine. X, when present, is preferably a neutral amino acid, preferably norleucine or leucine, or an alkylene or ethylene glycol containing amino acid linker according to the structure:

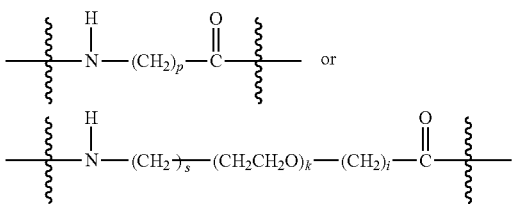

as shown above, where p, s, k and i are as otherwise described hereinabove. It is noted that compounds according to the present invention which contain an ABC amino acid linker (as opposed to those without a linker, i.e., n is 0) and especially a linker having at least one negatively charged amino acid (e.g., aspartic acid or glutamic acid), often exhibit less renal uptake and consequently enhanced pharmacokinetics (longer half-life in vivo) than do compounds according to the present invention which do not contain such linkers. AB linkers (where C is absent) wherein A is glycine or alanine, especially glycine and wherein B is glutamic acid or aspartic acid may also be preferred. In still other embodiments, ABC linkers wherein A is glycine, serine or norleucine, B is glycine, glutamic acid or aspartic acid and C is glutamic acid (especially when B is glycine) or norleucine (when B is glutamic acid or glycine) may also be preferred. In still other embodiments, when A and C are each absent, B is norleucine (Nle), leucine or isoleucine, preferably norleucine (Nle), in particular when m is 0 or X is a PEG linker (e.g. PEG2 linker) as otherwise described herein.

Alternatively, in certain embodiments, ABC may be preferably GlyGlyGly, GlySerGly, GlyGlyNle, GlyGluNle or NleGlyGlu. Preferred XABC groups (m and n are both 1) include, for example, GlyGlyGlyNle, GlySerGlyNle, GlyAspGlyNle, GlyGluGlyNle and PEG2Nle linkers.

$Y^1$ is preferably a radical of DOTA (1,4,7,10-tetraazacyclododecane-1,4,7,10-tetraacetic acid), CB-TE2A (4,11-bis(carboxymethyl)-1,4,8,11-tetraazabicyclo[6.6.2]hexadecane), NOTA (1,4,7-triazacyclononane-1,4,7-triacetic acid), DTPA (Diethylenetriaminopentaacetic acid), $MAG_3$ (Mercaptoacetyltriglycine) or 4,5-bis(2-mercaptoacetamido)pentanoic acid or HYNIC (hydrazinonicotinamide). More preferably, Y is a radical of DOTA, optionally complexed with a radioisotope as otherwise described herein.

In preferred embodiments, the present invention relates to the above compounds, including pharmaceutically acceptable salts, wherein the compound, especially the Y group, is complexed with a radioisotope (which may be a neutral species or a cationic species, and is preferably a polyvalent cationic species) selected from the group consisting of $^{86}Y$, $^{90}Y$, $^{111}In$, $^{177}Lu$, $^{225}Ac$, $^{212}Bi$, $^{213}Bi$, $^{66}Ga$, $^{67}Ga$, $^{68}Ga$, $^{64}Cu$, $^{67}Cu$, $^{71}As$ $^{72}As$, $^{76}As$, $^{77}As$, $^{65}Zn$, $^{48}V$, $^{203}Pb$, $^{209}Pb$, $^{212}Pb$, $^{166}Ho$, $^{149}Pm$, $^{153}Sm$, $^{201}Tl$, $^{188}Re$, $^{186}Re$ and $^{99m}Tc$.

In further preferred embodiments, $Y^1$ is a DOTA moiety which may be complexed with a radioisotope as indicated (this general structure also contemplates one or more carbonyl/carboxyl groups in the molecule also being complexed to the radioisotope and is non-limiting) according to the following:

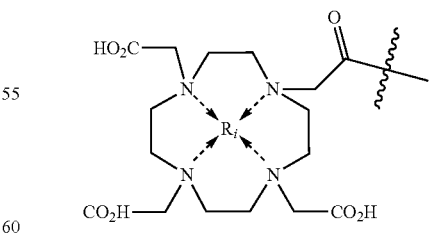

Where Ri is a radioisotope (which may be a neutral species or a cationic species, and is preferably a polyvalent cationic species) selected from the group consisting of $^{86}Y$, $^{90}Y$, $^{111}In$, $^{177}Lu$, $^{225}Ac$, $^{212}Bi$, $^{213}Bi$, $^{66}Ga$, $^{67}Ga$, $^{68}Ga$, $^{64}Cu$, $^{67}Cu$, $^{71}As$, $^{72}As$, $^{76}As$, $^{77}As$, $^{65}Zn$, $^{48}V$, $^{203}Pb$, $^{209}Pb$, $^{212}Pb$, $^{166}Ho$, $^{149}Pm$, $^{153}Sm$, $^{201}Tl$, $^{188}Re$, $^{186}Re$ and $^{99m}Tc$.

Radioisotopes are selected based on the physical half life, the decay mode (alpha, beta, auger, gamma, X-ray) and the energy of the radioisotope. In diagnostic aspects of the present invention, preferred radioisotopes include, for example, $^{111}$In, $^{86}$Y, $^{66}$Ga, $^{67}$Ga, $^{68}$Ga, $^{203}$Pb, $^{64}$Cu and $^{99m}$Tc.

Where compounds are to be analyzed using positron emission tomography or PET imaging they are labeled with a positron emitting radioisotopes such as: $^{66}$Ga, $^{68}$Ga, $^{64}$Cu, $^{86}$Y, or other polyvalent, cationic radiometals that decay by positron emission. In alternative embodiments, the compounds may be analyzed using single photon emission computed tomography or SPECT imaging when labeled with a gamma radiation emitting radioisotope which preferably includes $^{111}$In, $^{67}$Ga, $^{99m}$Tc and $^{203}$Pb or other gamma emitting radioisotope as disclosed herein.

The present invention relates to compounds and/or compositions which may be used to prepare imaging/therapeutic agents or as imaging/therapeutic agents (when complexed with a radioisotope) for diagnosing and treating melanoma, including metastatic melanoma as otherwise described herein. Compounds according to the present invention which are complexed with an appropriate radioisotope may be used to diagnose the existence and/or extent of melanoma, including metastatic melanoma, monitor therapy as a therapeutic aid of melanoma, including metastatic melanoma, and in certain instances, function as a therapeutic agent (peptide targeted radiation) for the treatment of melanoma, including metastatic melanoma.

The present invention also relates to pharmaceutical compositions comprising an effective amount of a compound according to the present invention which has been complexed with a radioisotope and combined with a carrier, additive or excipient in pharmaceutical dosage form as a diagnostic imaging agent or as a therapeutic agent. Compositions according to the present invention are formulated in pharmaceutical dosage form for administration preferably by a parenteral, preferably an intravenous route. Compositions according to the present invention may also be formulated for administration via a topical route, directly to the skin. Oral compositions may also be formulated for use in the present invention.

In the diagnostic method according to the present invention, a compound according to the present invention is administered to a patient, and evidence of elevated expression of MSH receptors in tissue of said patient through standard well-known nuclear imaging techniques, especially radiation (radionuclide) imaging, including scintigraphic imaging, and especially single photon emission computed tomography (SPECT) and positron emission tomography (PET) in comparison to a normal standard, is indicative of a disease state (melanoma) and extent of disease state (metastasis) in the tissue of the patient. The nuclear imaging techniques useful in the present diagnostic methods are well known in the art. In general, elevated levels of radiation emanating from a diagnosed tissue is evidence of elevated MSH receptor activity and indicative of a disease state or condition (melanoma and/or metastatic melanoma) wherein these receptors are found at elevated levels. Methods of diagnosing the existence and/or extent (stage) of melanoma, including metastatic melanoma are therefore additional aspects of the present invention. Thus, a diagnostic method of diagnosing the existence or absence of melanoma in a patient at risk for melanoma comprises administering to said patient a compound according to the present invention; imaging said patient to determine if tissue in said patient exhibits elevated expression of MSH receptors; and diagnosing said patient as having melanoma, including metastatic melanoma if said tissue evidences elevated expression of MSH receptors in comparison to a standard.

Methods of monitoring the treatment of melanoma, including metastatic melanoma in conjunction with traditional or experimental melanoma therapy is an additional aspect of the invention. In this aspect, a patient's response to therapy is monitored using the methods according to the present invention. In this method, a patient is monitored before and after therapy by administering compound according to the present invention and determining (through imaging diagnostics as otherwise described herein) the extent of expression of melanocyte stimulating hormone receptors in tissues of a patient before therapy and after therapy and comparing the expression levels with each other and/or with a standard (predetermined value) to determine the extent of reduction of cancer tissue which occurred pursuant to the therapeutic intervention.

Methods of treating melanoma represent a further aspect of the invention. In this aspect, compounds according to the present invention as described above are administered to a patient known to have melanoma and/or metastatic melanoma in effective amounts in order to reduce cancer tissue and otherwise treat the patient's cancer through targeted radiation therapy. The present therapeutic methods may be used alone or in combination with other treatment methods (surgery, chemotherapy, radiation therapy and/or immunotherapy (IL-2 and α-interferon) for melanoma/metastatic melanoma as otherwise disclosed herein. In preferred therapeutic method aspects of the present invention, compounds according to the present invention are labeled with $^{90}$Y, $^{177}$Lu, $^{186}$Re, $^{188}$Re, $^{212}$Bi/$^{212}$Pb, $^{213}$Bi, $^{149}$Pm, $^{166}$Ho and $^{153}$Sm and are administered to the patient (preferably intravenously or topically—i.e, directly onto the melanoma tissue in the skin of the patient) in order to target the malignant melanoma tumor, including metastatic melanoma tissue with radiation therapy.

DETAILED DESCRIPTION OF THE INVENTION

The following terms are used to describe the present invention. In the event that a term is not specifically defined herein, that term is accorded its commonly understood meaning within the context of its use by those of ordinary skill in the art. It is understood that the definitions of the terms which are used to describe the present invention are interpreted in a manner consistent with the present invention and within the context of a particular term's use in describing the present invention in one or more embodiments.

As used herein and in the appended claims, the singular forms "a," "an," and "the" include plural reference unless the context clearly dictates otherwise. Thus, for example, a reference to "a compound", within context, includes a plurality (for example, two or more compounds) of such elements, and so forth. Under no circumstances is the patent be interpreted to be limited to the specific examples or embodiments or methods specifically disclosed herein.

The term "patient" or "subject" is used throughout the specification to describe an animal, preferably a human, to whom treatment, including prophylactic treatment, with the compounds according to the present invention is provided. For treatment of those infections, conditions or disease states which are specific for a specific animal such as a human patient, the term patient refers to that specific animal.

The term "compound" is used herein to refer to any specific chemical compound disclosed herein. Within its use in context, the term generally refers to a single oligopeptide, or an oligopeptide bonded to a DOTA group optionally complexed with a radioisotope, but in certain instances may also refer to components/portions of such compounds, intermediates used to synthesize such compounds, stereoisomers and/or optical isomers (including racemic mixtures) of disclosed compounds. The term compound shall include, where applicable, any and all relevant pharmaceutically acceptable salts thereof.

The term "neutral amino acid" is an amino acid which has an uncharged sidechain at physiological pH. Neutral amino acids for use in the present invention include, for example, glycine, alanine, valine, leucine, isoleucine, norleucine, methionine, phenylalanine, serine, threonine and tyrosine. Preferred neutral amino acids include glycine, alanine, valine, leucine, isoleucine and norleucine. The term "negatively charged amino acid" is an amino acid which has a negatively charged sidechain at physiological pH. Preferred negatively charged amino acids for use in the present invention include glutamic acid and aspartic acid, both of which contain a plurality of carboxylate anions (in contrast to free/protonated carboxylic acids) at physiological pH.

The term "chelate", "chelator" or "chelating agent" is used to describe a moiety (as represented by $Y^1$ in generic structures) which is functionally capable of complexing or "chelating" a radioisotope as otherwise described herein. Each is appropriately chemically linked (via covalent linkers or directly to Cyclic peptides as otherwise described herein). Exemplary chelators for use in the present invention, which are well known in the art, include the following:

Polyaminocarboxylates, such as
EDTA: ethylenediaminetetraacetic acid
DTPA: diethylenetriaminepentaacetic acid
Polyaminocarboxylic Macrocycles, such as:
DOTA: 1,4,7,10-tetraazacyclododecane-1,4,7,10-tetraacetic acid
TRITA: 1,4,7,10-tetraazacyclotridecane-1,4,7,10-tetraacetic acid
TETA: triethylenetetramine bridged-cyclam-2a: 1,4,8,11-tetraazabicyclo[6.6.2]hexadecane-1,8-di(methanephosphonic acid)
DO3A: 1,4,7-tris(carboxymethyl)-1,4,7,10-tetraazacyclododecane
DO2A: 1,4,7,10-tetraazacyclododecane-1,7-bis(acetic acid)
Other Chelators, such as:
CB-TE2A (4,11-bis(carboxymethyl)-1,4,8,11-tetraazabicyclo[6.6.2]hexadecane)
NOTA (1,4,7-triazacyclononane-1,4,7-triacetic acid)
$MAG_3$ (Mercaptoacetyltriglycine)
4,5-bis(2-mercaptoacetamido)pentanoic acid
HYNIC (hydrazinonicotinamide)

Of the above chelators, DOTA is preferred, as is NOTA and HYNIC. The NOTA chelator is preferred especially when the radioisotope included is Cu or Ga. The HYNIC chelator is preferred, in particular when the radioisotope included is Tc and Re.

Chelates, chelators or chelating agents are generally bi- or multidentate ligands which generally produce a binding or complexation (complex) of a metal radioisotope as otherwise described herein. The ligand or chelator forms a chelate complex with the substrate. The term, without limitation, is used to describe complexes in which the metal ion is bound to two or more atoms of the chelating agent by whatever means (e.g., coordinate binding or complexation) occurs when a radioisotope and chelate group complex within each other in compounds according to the present invention. It is noted here that when a chelator is complexed to a radioisotope as used herein, the chelate complex structure is represented in a generic, nonlimiting sense, such that bonds which are represented may occur between a radioisotope and the chelating agent, as well as additional bonds (such as between carbonyl/carboxyl groups) which are not specifically represented, but which are understood/determined to be bonded within the context of the chelate complex (to accommodate that different radioisotopes may bind differently to different chelate groups).

The term "DOTA" is used as an abbreviation for 1,4,7, 10-tetraazacyclododecane-1,4,7,10-tetraacetic acid, a preferred chelator for use in the present invention, which chemical structure (bonded in compounds according to the present invention) is represented as follows:

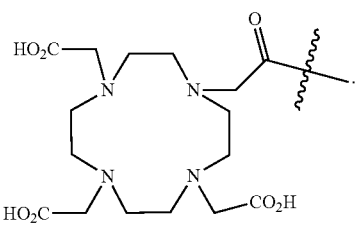 [SMILES: *C(=O)CN1CCN(CC(=O)O)CCN(CC(=O)O)CCN(CC(=O)O)CC1]

Complexed with radioisotopes according to the present invention, DOTA has the general (note that this general structure also includes the possibility of carbonyl/carboxyl groups also contributing to the complex depending on the radioisotope and is non-limiting) structure:

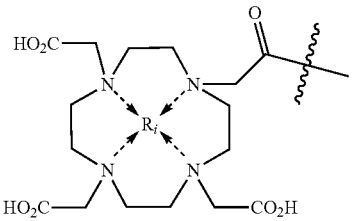

Where Ri is a radioisotope as otherwise disclosed herein.

The term "$CycMSH_{hex}$" or alternatively "cyclic peptide", "Cycpeptide" "cyclic MSHhex peptide", or refers to cyclic peptides which are bound optionally through a peptide linker (comprising 1, 2, 3 or 4 amino acid residues) to DOTA or other chelator according to the present invention. Cyclic peptides according to the present invention may be represented by the chemical structure:

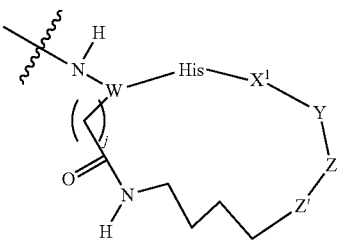

Wherein W is a C—H group from an aspartic acid or glutamic acid residue (preferably an aspartic acid residue), wherein the alkylene carboxylic acid sidechain of said aspartic acid or glutamic acid and the alkyleneamine sidechain of lysine are bonded together to form an amide linkage as indicated;

$X^1$ is phenylalanine, tyrosine or tryptophan, preferably phenylalanine;

Y is arginine or lysine, preferably arginine;

Z is tryptophan, phenylalanine or tyrosine, preferably tryptophan;

Z' is Lys(CONH$_2$) or Orn(CONH$_2$), preferably Lys(CONH$_2$);

j is 1 or 2 (preferably 1) or a pharmaceutically acceptable salt thereof,

In preferred aspects of the present invention, $X^1$ is D-phenylalanine, Y is arginine, Z is tryptophan Z' is Lys(CONH$_2$) and is represented by the following chemical structure:

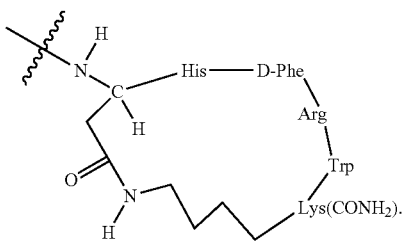

The term "radical" is used to describe a group which is covalently bonded to another group in compounds according to the present invention.

The term "acylated" is used to describe an acyl group which may be used, where appropriate, at a terminal amine group of compounds of the present invention. The term "acyl" is used throughout the specification to describe a group at a terminal amine position of an amino acid which contains a C$_0$ to C$_{20}$ (preferably a C$_0$ to C$_{20}$) linear, branched or cyclic alkyl chain. The acyl group at a terminal amine position, results in an amide linkage, which, after administration, may be cleaved. Acyl groups according to the present invention are represented by the structure:

where R$_4$ is H or a C$_0$ to C$_{20}$ (preferably, a C$_1$ to C$_{20}$) linear, branched or cyclic alkyl group, phenoxymethyl, aryl, alkoxy, alkoxyalkyl, aryloxyalkyl, alkoxycarbonyloxy groups (e.g., [(isopropoxycarbonyl)oxy]-methoxy), aryloxyalkyl, among others, all of which groups may be optionally substituted. Preferred acyl groups are those where R$_4$ is a C$_1$ to C$_{10}$ alkyl group. Acyl groups according to the present invention also include, for example, those acyl groups derived from benzoic acid and related acids, 3-chlorobenzoic acid, succinic, capric and caproic, lauric, myristic, palmitic, stearic and oleic groups, among numerous others. One of ordinary skill in the art will recognize the acyl groups which will have utility in the present invention, either to synthesize the target pharmaceutical compounds or as pro-drug forms of the nucleosides according to the present invention.

The term "melanoma" is used to describe a malignant tumor of melanocytes which are found predominantly in skin but also in the bowel and the eye (see uveal melanoma), even though melanoma can be found in any part of the body. Melanoma is a form of cancer that begins in melanocytes, the cells that make skin pigment, or melanin. It may begin in a mole (skin melanoma), but can also begin in other pigmented tissues. There are several types of melanoma, defined by where they first appear, including skin and eye melanoma and in rare instances in the GI tract or lymph nodes Melanoma is one of the rarer types of skin cancer but causes the majority of skin cancer related deaths. Malignant melanoma is a serious type of skin cancer. It is due to uncontrolled growth of pigment cells, called melanocytes. Despite many years of intensive laboratory and clinical research, the sole effective cure is surgical resection of the primary tumor before it achieves a Breslow thickness greater than 1 mm.

Around 160,000 new cases of melanoma are diagnosed worldwide each year. About 48,000 melanoma related deaths occur worldwide per year. Malignant melanoma accounts for 75 percent of all deaths associated with skin cancer. The treatment includes surgical removal of the tumor; adjuvant treatment; chemo- and immunotherapy, or radiation therapy. The severity of melanoma is often characterized by the Clark level, which are for thin tumors and describe how deeply the cancer has spread into the skin, and the Breslow depth, which refers to the microscopic depth of tumor invasion.

The following stages are identified in the progression of the melanoma disease state. Melanoma progresses from an early stage (in situ) through an invasive stage, a high risk melanoma stage, a regional metastatic stage and a distant metastatic stage with varying degrees of survivability, as set forth below.

Melanoma Stages:

Stage 0: Melanoma in Situ (Clark Level I), 99.9% Survival

Stage I/II: Invasive Melanoma, 85-95% Survival

T1a: Less than 1.00 mm primary, w/o Ulceration, Clark Level II-III

T1b: Less than 1.00 mm primary, w/Ulceration or Clark Level IV-V

T2a: 1.00-2.00 mm primary, w/o Ulceration

Stage II: High Risk Melanoma, 40-85% Survival

T2b: 1.00-2.00 mm primary, w/Ulceration

T3a: 2.00-4.00 mm primary, w/o Ulceration

T3b: 2.00-4.00 mm primary, w/Ulceration

T4a: 4.00 mm or greater primary w/o Ulceration

T4b: 4.00 mm or greater primary w/Ulceration

Stage III: Regional Metastasis, 25-60% Survival

N1: Single Positive Lymph Node

N2: 2-3 Positive Lymph Nodes OR Regional Skin/In-Transit Metastasis

N3: 4 Positive Lymph Nodes OR Lymph Node and Regional Skin/In Transit Metastases Stage IV: Distant Metastasis, 9-15% Survival M1a: Distant Skin Metastasis, Normal LDH M1b: Lung Metastasis, Normal LDH M1c: Other Distant Metastasis OR Any Distant Metastasis with Elevated LDH Based Upon AJCC 5-Year Survival with Proper Treatment Tradition therapy of melanoma involves a number of treatment options. These generally include surgery, chemotherapy, radiation therapy and immunotherapy (IL-2, other). In the case of surgery, treatment can vary and can include local excision, wide local excision, lymphadenectomy, sentinel lymph node biopsy and skin grafting. In the case of chemotherapy, a standard chemotherapeutic agent dacarbazine (DTIC) is administered to the patient in order to treat the cancer, generally through cancer cell death. In the case of radiation therapy, radiation is used as a palliative rather than a cure for melanoma. Radiation relieves bone pain and other symptoms caused by metastases to the bones, brain, and organs such as the liver. Although not curative, radiation treatment is being investigated for more widespread use in controlling other symptoms of skin cancer. In the case of immunotherapy (biologic treatment), a patient's natural immune system is raised or other immune compositions (IL-2) are administered to the patient against the cancer.

"Metastatic melanoma" refers to a progressed form of melanoma wherein the original cancer has metastasized to another area of the skin (regional or distant) or to other non-skin tissue (e.g., lungs, liver, brain, lymph system). Metastatic melanoma describes when melanoma has spread into surrounding healthy tissue and through the bloodstream, or lymphatic system, to other parts of the body. If melanoma spreads to these other areas, the cancer cells in the new tumor are still melanoma cells but the disease is called metastatic melanoma.

Unlike early stages of melanoma, which can be treated successfully with early diagnosis, the prognosis for patients diagnosed with metastatic melanoma is poor, with survival rates of six to nine months. In the past 35 years, the FDA has only approved two types of therapies for metastatic melanoma-interleukin 2 (IL-2) and DTIC. The methods of treatment for metastatic melanoma include radiation, immunotherapy, chemotherapy and palliative surgery. Currently, there are no approved therapies that significantly improve survival for patients with metastatic melanoma.

The term "imaging", "molecular imaging" or "radioimaging is used to describe methods that use the nuclear properties of matter in diagnosis and therapy, pursuant to the present invention. More specifically, the present invention relies on molecular imaging because it produces images that reflect biological processes that take place at the cellular and subcellular level.

Molecular imaging is a discipline that unites molecular biology and in vivo imaging. It enables the visualisation of the cellular function and the follow-up of the molecular process in living organisms without perturbing them. The multiple and numerous potentialities of this field are applicable to the diagnosis and treatment of diseases such as cancer, in the present invention, in particular, melanoma, including metastatic melanoma. This technique also contributes to improving the treatment of these disorders by optimizing the pre-clinical and clinical tests of new medication. This approach also has a major economic impact due to earlier and more precise diagnosis.

Molecular imaging differs from traditional imaging in that probes labeled biomarkers are used to help image particular targets or pathways. Biomarkers interact chemically with their surroundings and in turn alter the image according to molecular changes occurring within the area of interest. This process is markedly different from previous methods of imaging which primarily imaged differences in qualities such as density or water content. This ability to image fine molecular changes opens up an incredible number of exciting possibilities for medical application, including early detection and treatment of disease, in particular, melanoma and metastatic melanoma according to the present invention.

There are a number of different imaging modalities that can be used for noninvasive molecular imaging, using compounds according to the present invention. Each has different strengths and weaknesses and some are more adept at imaging multiple targets or sites than others. This is important in instances where metastatic melanoma is suspected. The modalities which can be used in the present invention are varied and in the present invention principally include single photon emission computed tomography (SPECT) and positron emission tomography (PET), discussed below.

The main purpose of SPECT when used in melanoma imaging pursuant to the present invention is to measure the distribution of radioisotope in skin tissue, in particular, those skin regions and other tissues where melanoma, including metastatic melanoma, is suspected. The development of computed tomography in the 1970s allowed mapping of the distribution of the radioisotopes in tissue, and led to the technique now called SPECT.

The imaging agent used in SPECT emits gamma rays, as opposed to the positron emitters used in PET. There are a number of radioisotopes (such as $^{99m}$Tc, $^{111}$In, $^{123}$I, $^{201}$Tl, $^{67}$Ga, $^{99m}$Tc and $^{203}$Pb, among other gamma ray emitters) that can be used in the present invention and imaged with SPECT technology. In SPECT, where possible, by rotating the gamma camera around the area to be analysed, a three dimensional image of the distribution of the radiotracer may be obtained by employing filtered back projection or other tomographic techniques. The radioisotopes used in SPECT have relatively long half lives (a few hours to a few days) making them easy to produce and relatively cheap in comparison to other radioisotopes. This represents the major advantage of SPECT as an imaging technique, since it is significantly cheaper than PET or other imaging methods such as magnetic resonance imaging (MRI). However, SPECT sometimes lacks exceptional spatial (i.e., where exactly the particle is) or temporal (i.e., did the contrast agent signal happen at a particular millisecond or not) resolution.

Another imaging technique which finds particular use in the present invention is positron emission tomography (PET). In PET, a molecule is tagged with a positron emitting isotope. These positrons (β particles) interact with nearby electrons, emitting two 511,000 eV photons, directed 180 degrees apart in opposite directions. These photons are then detected by the scanner which can estimate the density of positron annihilations in a specific area. When enough interactions and annihilations have occurred, the density of the original molecule may be measured in that area. Typical isotopes include $^{11}$C, $^{13}$N, $^{15}$O, $^{18}$F, $^{64}$Cu, $^{62}$Cu, $^{124}$I, $^{76}$Br, $^{82}$Rb and $^{68}$Ga, among others, including the preferred $^{66}$Ga, $^{68}$Ga, $^{64}$Cu, $^{86}$Y. One of the major disadvantages of PET is that most of the radioisotopes must be made with a cyclotron, thus making the use of PET, in certain instances prohibitively expensive. Most of these probes also have a half life measured in minutes and hours, thus forcing the cyclotron, in many instances, to be on site. These factors can make PET sometimes prohibitively expensive, except in certain cases, which the present invention addresses in certain aspects. PET imaging does have many advantages though. First and foremost is its sensitivity: a typical PET scanner can detect between $10^{-11}$ mol/L to $10^{-12}$ mol/L concentrations.

The term "effective" is used, to describe an amount of a compound, component or composition, which produces an intended effect when used within the context of its use, which may be a diagnostic method, a therapeutic method, a method to monitor the progression of therapy or other method (chemical synthesis) pursuant to the present invention. In the case of therapeutic methods, an effective amount for treating melanoma, including metastatic melanoma, is that amount which shrinks cancerous tissue (e.g., tumor), produces a remission, prevents further growth of the tumor and/or reduces the likelihood that the cancer in its early stages (in situ or invasive) does not progress further to metastatic melanoma.

Noted here is that within the context of the use of the present invention, the patient will be receiving a radiation dose, which provides guidance to the amount of compound which is considered effective when used within the context of its use. A patient undergoing a nuclear medicine procedure will receive a radiation dose. Under present international guidelines it is assumed that any radiation dose, however small, presents a risk. The radiation doses delivered to a patient in a nuclear medicine investigation present a very small risk of side effects, including inducing cancer in the patient. In this respect it is similar to the risk from X-ray investigations except that the dose is delivered internally rather than from an external source such as an X-ray machine.

The radiation dose from a diagnostic nuclear medicine procedure is expressed as an effective dose with units of sieverts (usually given in millisieverts, mSv). The effective dose resulting from an investigation is influenced by the amount of radioactivity administered in megabecquerels (MBq), the physical properties of the radiopharmaceutical used, its distribution in the body and its rate of clearance from the body.

Effective doses can range from 6 μSv (0.006 mSv) for a 3 MBq chromium-51 EDTA measurement of glomerular filtration rate to 37 mSv or more for a 150 MBq thallium-201 non-specific tumour imaging procedure. The common bone scan with 600 MBq of technetium-99m-MDP has an effective dose of 3 mSv. Formerly, units of measurement were the Curie (Ci), being 3.7E10 Bq, and also 1.0 grams of radium (Ra-226); the rad (radiation absorbed dose), now replaced by the Gray; and the rem (röntgen equivalent man), now replaced with the Sievert. The rad and rem are essentially equivalent for almost all nuclear medicine procedures, and only alpha radiation will produce a higher Rem or Sv value, due to its much higher relative biological effectiveness (RBE).

The term "coadministration" or "combination therapy" is used to describe a therapy in which at least two active compounds (one of which is a compound according to the present invention) in effective amounts are used to treat melanoma, including metastatic melanoma as otherwise described herein at the same time. Although the term coadministration preferably includes the administration of two active compounds to the patient at the same time, it is not necessary that the compounds be administered to the patient at the same time, although effective amounts of the individual compounds will be present in the patient at the same time. Compounds according to the present invention may be administered with one or more compound including a chemotherapeutic agent such as dacarbazine (DTIC) and/or and immunotherapeutic agent such as IL-2 and/or α-interferon, among other compounds.

The term "treating" or "successfully treating" when used in the context of treating melanoma, including metastatic melanoma, shall include shrinking a tumor, curing melanoma, including melanoma which has metastasized (by causing a remission of the cancer in the patient) or reducing the likelihood or preventing the spread of the melanoma into other organs. Melanoma, including metastatic melanoma, may be treated using compounds according to the present invention alone, or in combination with other methods and/or compounds including surgery, chemotherapy (especially the use of the chemotherapeutic agent dacarbazine or DTIC), radiation therapy (i.e., with agents other than the present therapeutic compositions) and immunotherapy (IL-2 and/or α-interferon).

In certain aspects of the invention, where the basic compound and in particular, the DOTA group, as described above, is complexed with a radioisotope for purposes of being used in the diagnosis or therapy of melanoma, including metastatic melanoma, the invention relates to compounds and their pharmaceutically acceptable salts according to the general chemical structure (note that the radioisotope may be complexed to one or more carbonyl/carboxyl groups of the DOTA moiety as well):

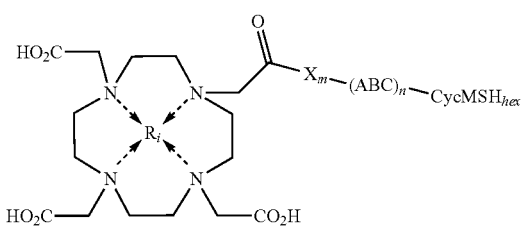

Where X, A, B, C, m, n and CycMSH$_{hex}$ are as otherwise described hereinabove; and the radioisotope ($R_1$) is selected from the group consisting of $^{86}$Y, $^{90}$Y, $^{111}$In, $^{177}$Lu, $^{225}$Ac, $^{212}$Bi, $^{213}$Bi, $^{66}$Ga, $^{67}$Ga, $^{68}$Ga, $^{64}$Cu, $^{67}$Cu, $^{71}$As, $^{72}$As, $^{76}$As, $^{77}$As, $^{65}$Zn, $^{48}$V, $^{203}$Pb, $^{209}$Pb, $^{212}$Pb, $^{166}$Ho, $^{149}$Pm, $^{153}$Sm, $^{201}$Tl, $^{188}$Re, $^{186}$Re and $^{99m}$Tc, or a pharmaceutically acceptable salt thereof.

Preferred compounds according to the present invention relate to compounds according to the structure (note that the radioisotope may be complexed to one or more carbonyl/carboxyl groups of the DOTA moiety as well):

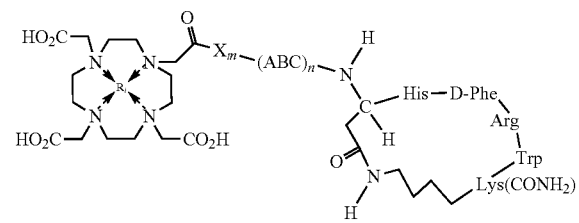

Where X, A, B, C, m, n and $R_1$ are the same as described above.

Additional preferred compounds according to the present invention may be represented by the following structure (note that the radioisotope may be complexed to one or more carbonyl/carboxyl groups of the DOTA moiety as well):

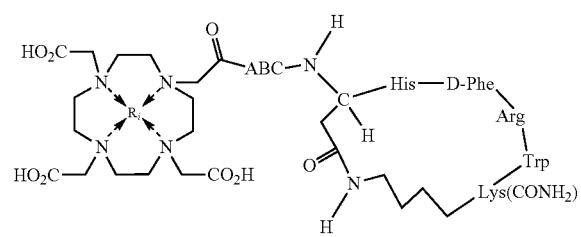

Where Ri is the same as described above and ABC is a diamino acid linker (A or C is not present) comprising two amino acids selected from the group consisting of neutral amino acids, negatively charged amino acids or mixtures thereof, and which may be preferably selected from the group consisting of GlyGly, LeuGlu, LeuAsp, NleGlu, NleAsp, GlyGlu, GlyAsp, GluGlu, GluAsp, AspGlu and AspAsp, or a pharmaceutically acceptable salt thereof. Alternatively, ABC may be preferably GlyGlyGly, GlySerGly, GlyGlyNle, GlyGluNle or NleGlyGlu, as well as GlyGlyGlyNle, GlySerGlyNle, GlyAspGlyNle, GlyGluGlyNle and PEG2Nle linkers.

In certain embodiments, the linker X is preferably

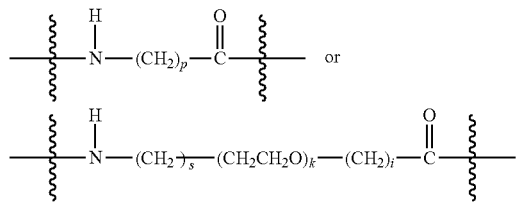

Wherein p is 2 to 8, k is 1 to 4 (more preferably 1 or 2), s is 0, 1 or 2 (more preferably 0) and i is 1 or 2.

Alternative preferred compounds according to the present invention are represented by the chemical structure (note that the radioisotope may be complexed to one or more carbonyl/carboxyl groups of the DOTA moiety as well):

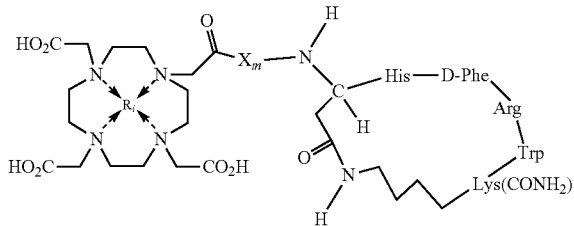

Wherein X is a neutral amino acid, preferably leucine or norleucine, preferably norleucine (Nle), m is 1 or 2 and $R_1$ is the same as otherwise described above, or a pharmaceutically acceptable salt thereof.

In preferred aspects, $R_i$ is selected from the group consisting of $^{111}$In, $^{86}$Y, $^{66}$Ga, $^{67}$Ga, $^{68}$Ga, $^{203}$Pb, $^{64}$Cu and $^{99m}$Tc when the compounds are to be used diagnostically or to monitor therapeutic intervention and is selected from the group consisting of $^{90}$Y, $^{177}$Lu, $^{186}$Re, $^{188}$Re, $^{212}$Bi/$^{212}$Pb, $^{213}$Bi, $^{149}$Pm, $^{166}$Ho and $^{153}$Sm when compounds according to the present invention are used in radiation therapy to treat melanoma, including metastatic melanoma.

The present invention also relates to pharmaceutical compositions comprising an effective amount of a compound for diagnostic and/or therapeutic purposes in combination with a pharmaceutically acceptable carrier, additive or excipient in pharmaceutical dosage form. For diagnostic purposes pharmaceutical compositions are formulated generally in parenteral dosage form, especially for intravenous administration, although oral or topical formulations may be useful in certain instances. In the case of the use of compounds according to the present invention for therapeutic purposes, the compositions are formulated preferably in parenteral or topical dosage forms, although orally administered dosage forms are also useful.

The compounds of the present invention, may, in accordance with the invention, be administered in single or divided doses by the oral, parenteral or topical routes. Administration of the active compound may range from a single intravenous injection to continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present invention as sprays, mists, or aerosols for intra-nasal, intra-tracheal or pulmonary administration may also be used. The present invention therefore also is directed to pharmaceutical compositions comprising an effective amount of compound according to the present invention, optionally in combination with a pharmaceutically acceptable carrier, additive or excipient.

The amount of compound used is that amount effective within the context of the administration, whether that administration is for diagnostic purposes or therapeutic purposes. A suitable oral dosage for a compound according to the present invention would be in the range of about 0.01 mg to 10 g or more per day, preferably about 0.1 mg to about 1 g per day. In parenteral formulations, a suitable dosage unit may contain from 0.1 to 250 mg of said compounds, which may be administered from one to four times per day (for diagnostic purpose, preferably once in a bolus dose), whereas for topical administration, formulations containing 0.01 to 1% active ingredient are preferred. It should be understood, however, that the dosage administration from patient to patient will vary and the dosage for any particular patient will depend upon the clinician's judgment, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier, additive or excipient material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like.

The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound according to the present invention can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds. In certain preferred diagnostic and/or therapeutic embodiments, compounds according to the present invention are administered intravenously in sterile saline solution.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Preservatives added may include benzalkonium chloride, chloro-butanol or phenylethyl alcohol, among numerous others.

Additionally, the compounds provided by the invention can be administered by suppository.

In certain aspects according to the present invention, where various cancers are to be treated, the compounds may be co-administered with at least one other anti-cancer agent such as dacarbazine (DTIC) or an immunotherapeutic agent such as IL-2 and/or α-interferon. In addition, compounds according to the present invention may be administered prior to, during or after surgery to remove melanoma tissue.

Preparation of compounds according to the present invention proceeds using standard synthetic chemical techniques which are readily available in the art. Synthetic methods for obtaining compounds related to the present invention may be found in the examples section of the present specification. These methods can serve as guides for obtaining compounds according to the present invention. In general, the present compounds may be made by condensing an activated DOTA or other chelating group (containing a leaving group or using a coupling agent to facilitate the binding of the carboxyl group on DOTA or other chelating group to the amine terminal group of the amino acid linker (including, in certain cases, the lysine side chain amine group) or, in the case where the linker is absent directly to the amine group of the cyclic peptide (CycMSH$_{hex}$). The radionuclide may be complexed to the chelate (DOTA) group either before or after the activated chelate (DOTA) group is condensed onto the linker-Cyclic peptide or directly onto the Cyclic peptide (linker not present). The linker-cyclic peptide and/or the cyclic peptide with no linker is synthesized using conventional peptide synthesis (as otherwise described in the examples section or using methods readily available in the art using protecting group chemistry) and the various condensation and other reactions, etc. are readily performed using methods described herein or otherwise as readily known in the art. See FIG. 2 hereof for a preferred synthetic approach. Other approaches will be readily recognized to those of ordinary skill.

Once the compounds are synthesized, they may be formulated in pharmaceutical dosage form using convention pharmaceutical formulation methods readily available in the art by simply admixing compounds with chosen carriers, additives and/or excipients, depending upon the dosage form to be used and depending upon the use (diagnostic or therapeutic) of the compositions.

The following examples are provided to assist in describing the present invention. The details of these examples and the general description of the examples are for description purposes only and should be seen or taken to limit the scope of the invention in any way.

Examples—First Set

Materials and Methods
Chemicals and Reagents

Amino acid and resin were purchased from Advanced ChemTech Inc. (Louisville, Ky.) and Novabiochem (San Diego, Calif.). DOTA-tri-t-butyl ester was purchased from Macrocyclics Inc. (Richardson, Tex.). $^{111}$InCl$_3$ was purchased from Trace Life Sciences, Inc. (Dallas, Tex.). $^{125}$I-Tyr$^2$-[Nle$^4$, D-Phe$^7$]-α-MSH {$^{125}$I-(Tyr$^2$)-NDP-MSH} was obtained from PerkinElmer, Inc. (Waltham, Mass.). All other chemicals used in this study were purchased from Thermo Fischer Scientific (Waltham, Mass.) and used without further purification. B16/F1 melanoma cells were obtained from American Type Culture Collection (Manassas, Va.).

Peptide Synthesis

DOTA-Nle-CycMSH$_{hex}$ was synthesized using standard fluorenylmethyloxycarbonyl (Fmoc) chemistry. Briefly, intermediate scaffold of (tBu)$_3$DOTA-Nle-Asp(O-2-PhiPr)-His(Trt)-DPhe-Arg(Pbf)-Trp(Boc)-Lys(Dde) was synthesized on H$_2$N-Sieber amide resin by an Advanced ChemTech multiple-peptide synthesizer (Louisville, Ky.). The protecting group of Dde was removed by 2% hydrazine for peptide cyclization. The protecting group of 2-phenylisopropyl was removed and the protected peptide was cleaved from the resin treating with a mixture of 2.5% of trifluoroacetic acid (TFA) and 5% of triisopropylsilane for 1 h. After the precipitation with ice-cold ether and characterization by liquid chromatography-mass spectroscopy (LC-MS), the protected peptide was dissolved in H$_2$O/CH$_3$CN (30:70) and lyophilized to remove the reagents such as TFA and triisopropylsilane. The protected peptide was further cyclized by coupling the carboxylic group from the Asp with the epsilon amino group from the Lys. The cyclization reaction was achieved by an overnight reaction in dimethylformamide (DMF) using benzotriazole-1-yl-oxy-tris-pyrrolidino-phosphonium-hexafluorophosphate (PyBOP) as a coupling agent in the presence of N,N-diisopropylethylamine (DIEA). After the characterization by LC-MS, the cyclized protected peptide was dissolved in H$_2$O/CH$_3$CN (30:70) and lyophilized to remove the reagents such as PyBOP and DIEA. The protecting groups were totally removed by treating with a mixture of trifluoroacetic acid (TFA), thioanisole, phenol, water, ethanedithiol and triisopropylsilane (87.5:2.5:2.5:2.5:2.5:2.5) for 4 h at room temperature (25° C.). The peptide was precipitated and washed with ice-cold ether four times, purified by reverse phase-high performance liquid chromatography (RP-HPLC) and characterized by LC-MS.

In Vitro Competitive Binding Assay

The IC$_{50}$ value of DOTA-Nle-CycMSH$_{hex}$ was determined by in vitro competitive binding assay according to our previously published procedure (19). B16/F1 cells were harvested and seeded into a 24-well cell culture plate (5×10$^5$ cells/well) and incubated at 37° C. overnight. After being washed twice with binding medium {Dulbecco's Modified Eagle's Medium with 25 mM N-(2-hydroxyethyl)-piperazine-N'-(2-ethanesulfonic acid), pH 7.4, 0.2% bovine serum albumin (BSA), 0.3 mM 1,10-phenathroline}, the cells were incubated at room temperature (25° C.) for 2 h with approximately 60,000 cpm of $^{125}$I-Tyr$^2$-NDP-MSH in the presence of increasing concentrations ($10^{-12}$ to $10^{-5}$ M) of DOTA-Nle-CycMSH$_{hex}$ in 0.3 mL of binding medium. The reaction medium was aspirated after the incubation. The cells were rinsed twice with 0.5 mL of ice-cold pH 7.4, 0.2% BSA/0.01 M phosphate buffered saline (PBS) and lysed in 0.5 mL of 1 N NaOH for 5 minutes. The activities associated with cells were measured in a Wallac 1480 automated gamma counter (PerkinElmer, N.J.). The IC$_{50}$ value of the peptide was calculated using Prism software (GraphPad Software, La Jolla, Calif.).

Peptide Radiolabeling with $^{111}$In $^{111}$In-DOTA-Nle-CycMSH$_{hex}$ was prepared in a 0.5 M NH$_4$OAc-buffered solution at pH 4.5 according to our published procedure (19). Briefly, 50 μl of $^{111}$InCl$_3$ (37-74 MBq in 0.05 M HCl aqueous solution), 10 μL of 1 mg/mL DOTA-Nle-CycMSH$_{hex}$ aqueous solution and 400 μL of 0.5 M NH$_4$OAc (pH 4.5) were added into a reaction vial and incubated at 75° C. for 45 min. After the incubation, 10 μL of 0.5% EDTA aqueous solution was added into the reaction vial to scavenge potential unbound $^{111}$In$^{3+}$ ions. The radiolabeled peptide was purified to single species by Waters RP-HPLC (Milford, Mass.) on a Grace Vydac C-18 reverse phase analytical column (Deerfield, Ill.) using a 20-minute gradient of 18-28% acetonitrile in 20 mM HCl aqueous solution with a flow rate of 1.0 mL/min. Purified peptide sample was purged with N$_2$ gas for 20 minutes to remove the acetonitrile. The pH of final solution was adjusted to 7.4 with 0.1 N NaOH and sterile normal saline for animal studies. In vitro serum stability of $^{111}$In-DOTA-Nle-CycMSH$_{hex}$ was determined by incubation in mouse serum at 37° C. for 24 h and monitored for degradation by RP-HPLC.

Cellular Internalization and Efflux of $^{111}$In-DOTA-Nle-CycMSH$_{hex}$ Cellular internalization and efflux of $^{111}$n-DOTA-Nle-CycMSH$_{hex}$ were evaluated in B16/F1 melanoma cells. After being washed twice with the binding medium, the B16/F1 cells seeded in cell culture plates were incubated at 25° C. for 20, 40, 60, 90 and 120 mM (n=3) in the presence of approximate 200,000 counts per minute (cpm) of HPLC-purified $^{111}$1n-DOTA-Nle-CycMSH$_{hex}$. After incubation, the reaction medium was aspirated and the cells were rinsed with 2×0.5 mL of ice-cold pH 7.4, 0.2% BSA/0.01 M PBS. Cellular internalization of $^{111}$In-DOTA-Nle-CycMSH$_{hex}$ was assessed by washing the cells with acidic buffer [40 mM sodium acetate (pH 4.5) containing 0.9% NaCl and 0.2% BSA] to remove the membrane-bound radioactivity. The remaining internalized radioactivity was obtained by lysing the cells with 0.5 mL of 1 N NaOH for 5 min. Membrane-bound and internalized $^{111}$In activities were counted in a gamma counter. Cellular efflux of $^{111}$In-DOTA-Nle-CycMSH$_{hex}$ was determined by incubating the B16/F1 cells with $^{111}$In-DOTA-Nle-CycMSH$_{hex}$ for 2 h at 25° C., removing non-specific-bound activity with 2×0.5 mL of ice-cold PBS rinse, and monitoring radioactivity released into cell culture medium. At time points of 20, 40, 60, 90 and 120 min, the radioactivities on the cell surface and inside the cells were separately collected and counted in a gamma counter.

Biodistribution Studies

All the animal studies were conducted in compliance with Institutional Animal Care and Use Committee approval. The mice were housed five animals per cage in sterile microisolator cages in a temperature- and humidity-controlled room with a 12-h light/12-h dark schedule. The pharmacokinetics of $^{111}$In-DOTA-Nle-CycMSH$_{hex}$ was determined in B16/F1 melanoma-bearing C57 female mice (Harlan, Indianapolis, Ind.). C57 mice were subcutaneously inoculated on the right flank with 1×10$^6$ B16/F1 cells. The weight of tumors reached approximately 0.2 g 10 days post cell inoculation. Each melanoma-bearing mouse was injected with 0.037 MBq of $^{111}$In-DOTA-Nle-CycMSH$_{hex}$ via the tail vein. Groups of 5 mice were sacrificed at 0.5, 2, 4 and 24 h post-injection, and tumors and organs of interest were harvested, weighed and counted. Blood values were taken as 6.5% of the whole-body weight. The tumor uptake specificity of $^{111}$In-DOTA-Nle-CycMSH$_{hex}$ was determined by co-injecting 10 μg of unlabeled NDP-MSH, a linear α-MSH peptide analogue with picomolar affinity for the MC1 receptor present on the melanoma cells. To examine whether L-lysine co-injection can reduce the renal uptake or not, a group of 5 mice were injected with a mixture of 12 mg of L-lysine and 0.037 MBq of $^{111}$In-DOTA-Nle-CycMSH$_{hex}$. The mice were sacrificed at 2 h post-injection. The tumor and organs of interest were harvested, weighed and counted.

Melanoma Imaging with $^{111}$In-DOTA-Nle-CycMSH$_{hex}$

Two B16/F1 melanoma-bearing C57 mice (10 days post the cell inoculation) were injected with 37.0 MBq of $^{111}$In-DOTA-Nle-CycMSH$_{hex}$ via the tail vein, respectively. The mice were sacrificed for small animal SPECT/CT (Nano-SPECT/CT®, Bioscan) imaging at 2 and 24 h post-injection. The 9-min CT imaging was immediately followed by the whole-body SPECT imaging. The SPECT scans of 24 projections were acquired and total acquisition time was approximately 60 mM. Reconstructed data from SPECT and CT were visualized and co-registered using InVivoScope (Bioscan, Washington D.C.).

Urinary Metabolites of $^{111}$In-DOTA-Nle-CycMSH$_{hex}$

The mouse used for the imaging study (2 h post-injection) described above was euthanized and the urine was collected for indentifying the metabolites. The urinary sample was centrifuged at 16,000 g for 5 min prior to the HPLC analysis. The radioactive metabolite in the urine was analyzed by injecting aliquots of urine into the HPLC. A 20-minute gradient of 18-28% acetonitrile/20 mM HCl was used for the urine analysis.

Statistical Analysis

Statistical analysis was performed using the Student's t-test for unpaired data. A 95% confidence level was chosen to determine the significance between the tumor uptakes of $^{111}$In-DOTA-Nle-CycMSH$_{hex}$ with or without NDP-MSH co-injection, and between the renal uptakes of $^{111}$In-DOTA-Nle-CycMSH$_{hex}$ with or without L-lysine co-injection in the biodistribution studies described above. Differences at the 95% confidence level (p<0.05) were considered significant.

Results

Figure 2:
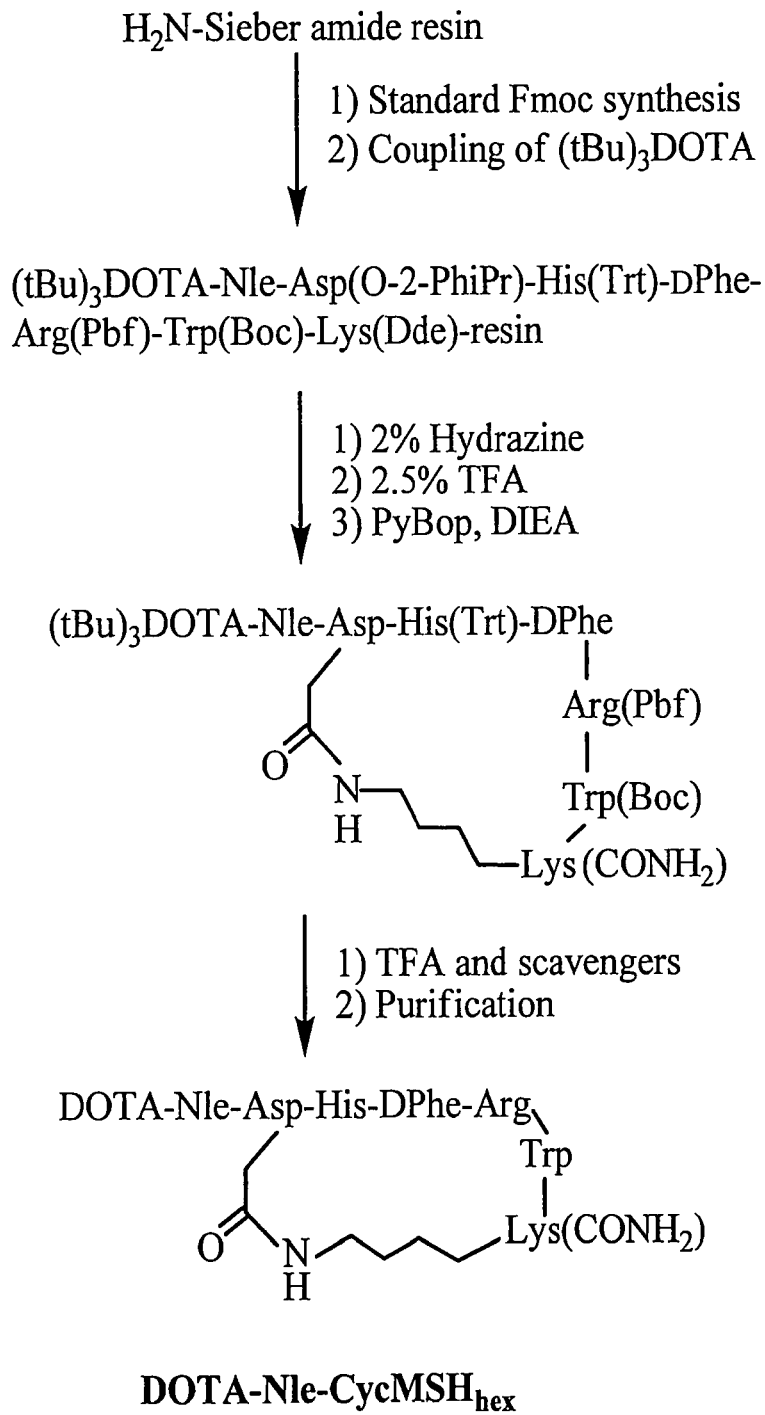
FIG. 2 shows the synthetic scheme of DOTA-Nle-CycMSH$_{hex}$.

To examine the profound effect of the peptide ring size on the melanoma and kidney uptakes of the $^{111}$In-labeled lactam bridge-cyclized α-MSH peptide, a novel peptide of DOTA-Nle-CycMSH$_{hex}$ was synthesized and purified by RP-HPLC. The identity of the peptide was confirmed by electrospray ionization mass spectrometry (EIMS MW: 1368.5; Calculated MW: 1368.2). DOTA-Nle-CycMSH$_{hex}$ displayed greater than 95% purity with 30% overall synthetic yield. The schematic structures of DOTA-Nle-CycMSH$_{hex}$ and DOTA-GlyGlu-CycMSH are shown in FIG. 1. FIG. 2 illustrates the synthetic scheme of DOTA-Nle-CycMSH$_{hex}$. The competitive binding curve of DOTA-Nle-CycMSH$_{hex}$ is presented in FIG. 3A. The IC$_{50}$ value of DOTA-Nle-CycMSH$_{hex}$ was 1.77 nM in B16/F1 cells.

The peptide was readily labeled with $^{111}$In in 0.5 M ammonium acetate at pH 4.5 with greater than 95% radiolabeling yield. $^{111}$In-DOTA-Nle-CycMSH$_{hex}$ was completely separated from its excess non-labeled peptide by RP-HPLC. The retention time of $^{111}$In-DOTA-Nle-CycMSH$_{hex}$ was 10.7 min. $^{111}$In-DOTA-Nle-CycMSH$_{hex}$ showed greater than 98% radiochemical purity after the HPLC purification. $^{111}$In-DOTA-Nle-CycMSH$_{hex}$ was stable in mouse serum at 37° C. for 24 h. Only the $^{111}$In-DOTA-Nle-CycMSH$_{hex}$ was detected by RP-HPLC after 24 h of incubation.

Figure 3:
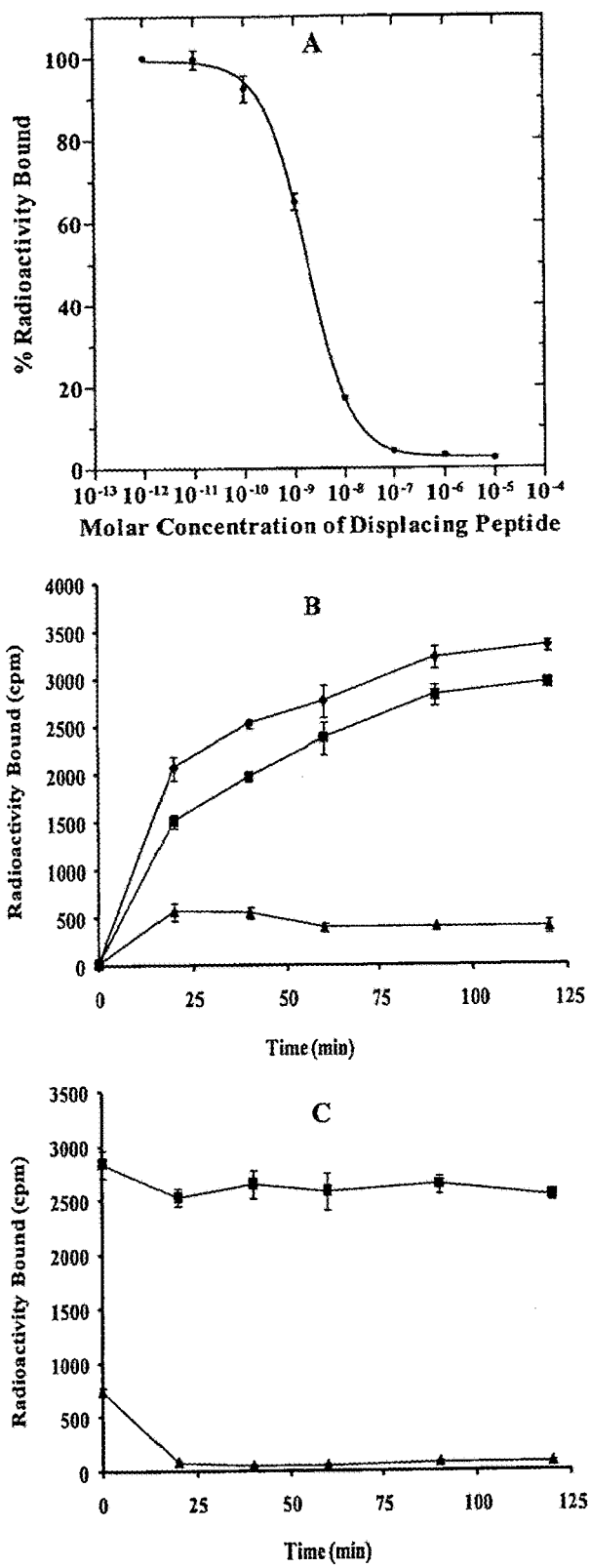
FIG. 3 shows the competitive binding curve (A) of DOTA-Nle-CycMSH$_{hex}$ in B16/F1 melanoma cells. The IC$_{50}$ value of DOTA-Nle-CycMSH$_{hex}$ was 1.77 nM. Cellular internalization (B) and efflux (C) of $^{111}$In-DOTA-Nle-CycMSH$_{hex}$ in B16/F1 melanoma cells at 25° C. Total bound radioactivity (♦), internalized activity (■) and cell membrane activity (▲) were presented as counts per minute (cpm).

Cellular internalization and efflux of $^{111}$In-DOTA-Nle-CycMSH$_{hex}$ were evaluated in B16/F1 cells. FIGS. 3B and 3C illustrate the cellular internalization and efflux of $^{111}$In-DOTA-Nle-CycMSH$_{hex}$. $^{111}$In-DOTA-Nle-CycMSH$_{hex}$ exhibited rapid cellular internalization and extended cellular retention. There were 72.9±3.5% and 88.3±0.7% of the cellular uptake of $^{111}$In-DOTA-Nle-CycMSH$_{hex}$ activity internalized in the B16/F1 cells at 20 and 120 min post incubation, respectively. Cellular efflux results demonstrated that 89.5±1.9% of internalized $^{111}$In-DOTA-Nle-CycMSH$_{hex}$ activity remained inside the cells 2 h after incubating cells in culture medium.

The melanoma targeting and pharmacokinetic properties of $^{111}$In-DOTA-Nle-CycMSH$_{hex}$ were determined in B16/F1 melanoma-bearing C57 mice. The biodistribution results of $^{111}$In-DOTA-Nle-CycMSH$_{hex}$ are shown in Table 1. $^{111}$In-radiolabeled NDP-MSH co-injection was only 4.2% of the tumor uptake without NDP-MSH co-injection at 2 h after dose administration (p<0.05), demonstrating that the tumor uptake was specific and MC1 receptor-mediated. Whole-body clearance of $^{111}$In-DOTA-Nle-CycMSH$_{hex}$ was rapid, with approximately 82% of the injected radioactivity cleared through the urinary system by 2 h post-injection (Table 1, below). Normal organ uptakes of $^{111}$In-DOTA-Nle-CycMSH$_{hex}$ were low (<1.89% ID/g) except for the kidneys at 2, 4 and 24 h post-injection. High tumor/blood and high tumor/normal organ uptake ratios were achieved as early as 0.5 h post-injection (Table 1). As the major excretion pathway of $^{111}$In-DOTA-Nle-CycMSH$_{hex}$, the kidney uptake value was 16.20±4.32% ID/g at 0.5 h post-injection and decreased to 9.31±0.91% ID/g at 24 h post-injection. The tumor to kidney uptake ratios of $^{111}$In-DOTA-Nle-CycMSH$_{hex}$ are presented in FIG. 4. The tumor/kidney uptake ratios of $^{111}$In-DOTA-Nle-CycMSH$_{hex}$ were 2.04, 1.70 and 1.13 at 2, 4 and 24 h post-injection. Co-injection of NDP-MSH didn't reduce the renal uptake of the $^{111}$In-DOTA-Nle-CycMSH$_{hex}$ activity at 2 h post-injection, indicating that the renal uptake was not MC1 receptor-mediated. Co-injection of L-lysine significantly (p<0.05) reduced the kidney uptake value by 30% at 2 h post-injection (Table 1).

TABLE 1

Biodistribution of $^{111}$In-DOTA-Nle-CycMSH$_{hex}$ in B16/F1 melanoma-bearing C57 mice. The data were presented as percent injected dose/gram or as percent injected dose (Mean ± SD, n = 5)

| Tissues | 0.5 h | 2 h | 4 h | 24 h | 2 h NDP blockade | 2 h L-lysine co-injection |
|---|---|---|---|---|---|---|
| Percent injected dose/gram (% ID/g) | | | | | | |
| Tumor | 24.94 ± 4.58 | 19.39 ± 1.65 | 17.01 ± 2.54 | 10.53 ± 1.11 | 0.81 ± 0.03* | 14.48 ± 3.25 |
| Brain | 0.21 ± 0.07 | 0.02 ± 0.01 | 0.06 ± 0.03 | 0.03 ± 0.01 | 0.01 ± 0.01 | 0.04 ± 0.01 |
| Blood | 3.33 ± 0.35 | 0.11 ± 0.07 | 0.05 ± 0.02 | 0.02 ± 0.01 | 0.07 ± 0.05 | 0.92 ± 0.48 |
| Heart | 1.24 ± 0.15 | 0.16 ± 0.10 | 0.12 ± 0.03 | 0.07 ± 0.05 | 0.06 ± 0.02 | 0.37 ± 0.02 |
| Lung | 2.45 ± 0.83 | 0.32 ± 0.10 | 0.10 ± 0.05 | 0.10 ± 0.03 | 0.30 ± 0.06 | 0.75 ± 0.21 |
| Liver | 2.75 ± 0.26 | 1.46 ± 0.20 | 1.72 ± 0.07 | 1.89 ± 0.14 | 1.46 ± 0.08 | 1.42 ± 0.30 |
| Spleen | 1.09 ± 0.33 | 0.41 ± 0.13 | 0.47 ± 0.13 | 0.32 ± 0.08 | 0.44 ± 0.02 | 0.43 ± 0.07 |
| Stomach | 3.20 ± 0.98 | 1.25 ± 0.24 | 1.49 ± 0.12 | 1.34 ± 0.42 | 0.36 ± 0.14 | 1.64 ± 0.78 |
| Kidneys | 16.20 ± 4.32 | 9.52 ± 0.44 | 9.99 ± 1.39 | 9.31 ± 0.91 | 11.56 ± 0.56 | 6.66 ± 0.62* |
| Muscle | 0.60 ± 0.22 | 0.15 ± 0.08 | 0.10 ± 0.08 | 0.03 ± 0.01 | 0.02 ± 0.01 | 0.10 ± 0.08 |
| Pancreas | 1.18 ± 0.38 | 0.14 ± 0.02 | 0.16 ± 0.02 | 0.23 ± 0.08 | 0.12 ± 0.02 | 0.21 ± 0.05 |
| Bone | 1.34 ± 0.40 | 0.18 ± 0.10 | 0.22 ± 0.15 | 0.16 ± 0.03 | 0.05 ± 0.04 | 0.55 ± 0.14 |
| Skin | 4.11 ± 0.72 | 0.66 ± 0.23 | 0.53 ± 0.05 | 0.64 ± 0.16 | 0.29 ± 0.02 | 1.02 ± 0.09 |
| Percent injected dose (% ID) | | | | | | |
| Intestines | 2.16 ± 0.28 | 1.40 ± 0.56 | 3.03 ± 1.06 | 1.41 ± 0.86 | 1.14 ± 0.47 | 1.85 ± 0.73 |
| Urine | 57.00 ± 3.91 | 82.23 ± 5.83 | 84.61 ± 5.21 | 87.29 ± 3.60 | 92.25 ± 1.56 | 76.79 ± 5.35 |
| Tumor to normal tissue uptake ratio | | | | | | |
| Tumor/Blood | 7.49 | 176.27 | 340.20 | 526.50 | 11.57 | 15.74 |
| Tumor/Kidneys | 1.54 | 2.04 | 1.70 | 1.13 | 0.07 | 2.17 |
| Tumor/Lung | 10.18 | 60.59 | 170.10 | 105.30 | 2.70 | 19.31 |
| Tumor/Liver | 9.07 | 13.28 | 9.89 | 5.57 | 0.55 | 10.20 |
| Tumor/Muscle | 41.57 | 129.27 | 170.10 | 351.00 | 40.50 | 144.80 |
| Tumor/Skin | 6.07 | 29.38 | 32.09 | 16.45 | 2.79 | 14.20 |

*P < 0.05, significance comparison between the tumor uptakes of $^{111}$In-DOTA-Nle-CycMSH$_{hex}$ with or without NDP-MSH blockade, and between the kidney uptakes of $^{111}$In-DOTA-Nle-CycMSH$_{hex}$ with or without L-lysine co-injection.

Figure 5:
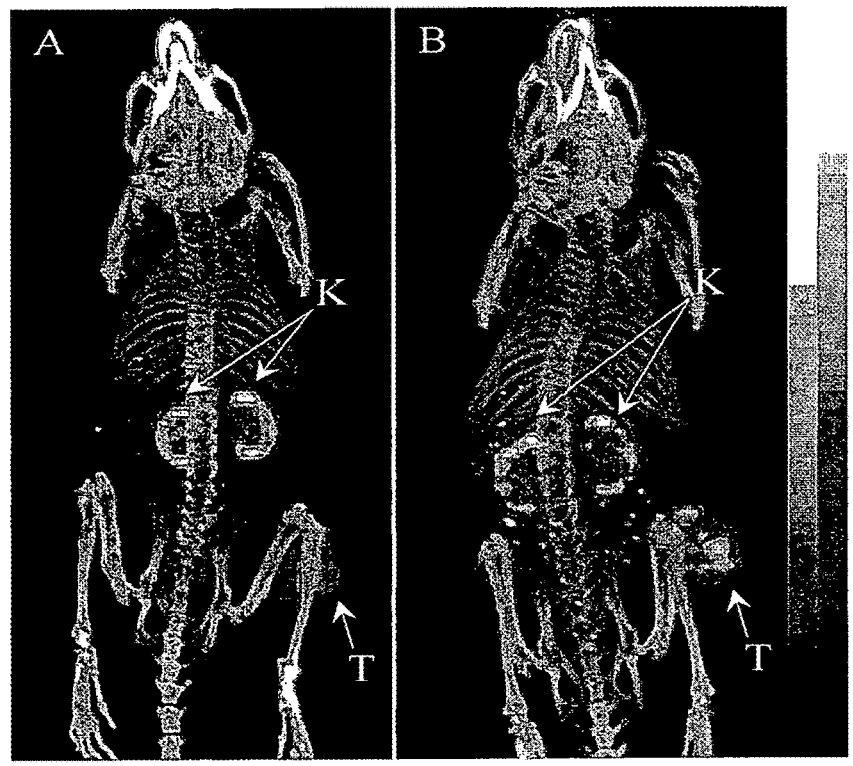
FIG. 5 shows whole-body SPECT/CT images of B16/F1 flank melanoma-bearing C57 mice at 2 (A) and 24 h (B) post-injection of 37.0 MBq of $^{111}$In-DOTA-Nle-CycMSH$_{hex}$. Tumor (T) and kidneys (K) are highlighted with arrows on the images. HPLC profile (C) of radioactive urine sample of a B16/F1 melanoma-bearing C57 mouse at 2 h post-injection of $^{111}$In-DOTA-Nle-CycMSH$_{hex}$. $^{111}$In-DOTA-Nle-CycMSH$_{hex}$ remained intact in the urine 2 h post-injection.
Figure 5:
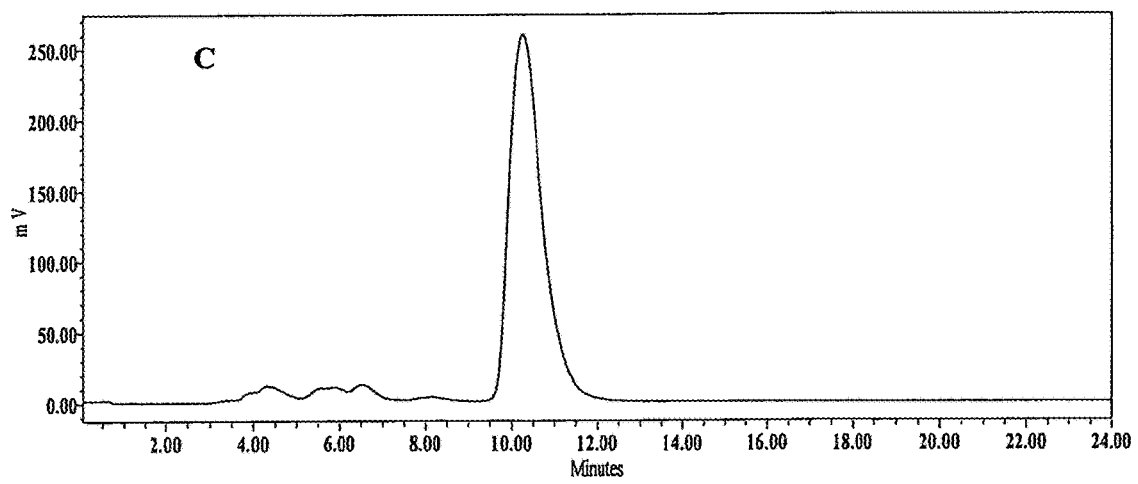

DOTA-Nle-CycMSH$_{hex}$ exhibited very rapid high melanoma uptake and prolonged tumor retention in melanoma-bearing mice. At 0.5 h post-injection, $^{111}$In-DOTA-Nle-CycMSH$_{hex}$ reached its peak tumor uptake value of 24.94±4.58% ID/g. There were 17.01±2.54% ID/g and 10.53±1.11% ID/g of the $^{111}$In-DOTA-Nle-CycMSH$_{hex}$ activity remained in the tumors at 4 and 24 h post-injection, respectively. In melanoma uptake blocking study, the tumor uptake of $^{111}$In-DOTA-Nle-CycMSH$_{hex}$ with 10 μg of non- Two B16/F1 melanoma-bearing C57 mice were separately injected with 37.0 MBq of $^{111}$In-DOTA-Nle-CycMSH$_{hex}$ through the tail vein to visualize the tumors at 2 and 24 h post dose administration. The whole-body SPECT/CT images are presented in FIGS. 5A and 5B. Flank melanoma tumors were clearly visualized by SPECT/CT at 2 and 24 h post-injection of $^{111}$In-DOTA-Nle-CycMSH$_{hex}$. Both images showed high tumor to normal organ uptake ratios except for the kidneys, which was coincident with the biodistribution results. Urinary metabolite of $^{111}$In-DOTA-Nle-CycMSH$_{hex}$ was analyzed by RP-HPLC 2 h post-injection. FIG. 5C illustrates the urinary HPLC profile of $^{111}$In-DOTA-Nle-CycMSH$_{hex}$. $^{111}$In-DOTA-Nle-CycMSH$_{hex}$ remained intact in the urine 2 h post-injection.

Discussion

Cyclization strategies using disulfide bridge, lactam bridge and metal coordination have been successfully employed to cyclize the α-MSH peptides to enhance the binding affinities and in vivo stabilities of the peptides (21-24). Both $^{111}$In-labeled metal-cyclized and lactam bridge-cyclized α-MSH peptides exhibited greater melanoma uptake and lower renal uptake values than those of $^{111}$In-labeled disulfide bridge-cyclized α-MSH peptide (19, 27). We have reported a novel class of melanoma-specific $^{111}$In-labeled lactam bridge-cyclized α-MSH peptides for both primary and metastatic melanoma imaging (19, 20). $^{111}$In-DOTA-GlyGlu-CycMSH (FIG. 1), with a 12-amino acid peptide ring, exhibited great potential as a melanoma-specific imaging probe in detecting both primary and metastatic melanoma lesions (19, 20). However, the tumor uptake value of $^{111}$In-DOTA-GlyGlu-CycMSH was 60.15% of the tumor uptake value of $^{111}$In-DOTA-Re(Arg$^{11}$)CCMSH, whereas the kidney uptake value of $^{111}$In-DOTA-GlyGlu-CycMSH was 1.5 times the renal uptake value of $^{111}$In-DOTA-Re(Arg$^{11}$)CCMSH at 2 h post-injection in B16/F1 melanoma-bearing C57 mice (17, 19). The structural differences between $^{111}$In-DOTA-GlyGlu-CycMSH and $^{111}$In-DOTA-Re(Arg$^{11}$)CCMSH (FIG. 1) indicated that smaller size of the peptide ring might contribute to the more favorable melanoma targeting and pharmacokinetic properties of $^{111}$In-DOTA-Re(Arg$^{11}$)CCMSH since there was a 8-amino acid peptide ring in $^{111}$In-DOTA-Re(Arg$^{11}$)CC-MSH whereas there was a 12-amino acid peptide ring in $^{111}$In-DOTA-GlyGlu-CycMSH. Moreover, It was reported that the lactam bridge-cyclized α-MSH peptide with a 6-amino acid peptide ring {Ac-Nle-c[Asp-His-DPhe-Arg-Trp-Lys(CONH$_2$)]} displayed not only higher MC1 receptor binding affinity, but also slower MC1 receptor dissociation rate than the native α-MSH peptide (25). Therefore, we synthesized a novel DOTA-conjugated lactam bridge-cyclized peptide with a 6-amino acid peptide ring {DOTA-Nle-CycMSH$_{hex}$} to examine the profound effect of the peptide ring size on the tumor and kidney uptakes in this study.

The conjugation of DOTA to the N-terminus of the peptide and the reduction of the peptide ring size did not sacrifice the MC1 receptor binding affinity of DOTA-Nle-CycMSH$_{hex}$. DOTA-Nle-CycMSH$_{hex}$ exhibited 1.77 nM MC1 receptor binding affinity in B16/F1 melanoma cells (FIG. 3A). $^{111}$In-DOTA-Nle-CycMSH$_{hex}$ displayed rapid internalization and prolonged retention in B16/F1 melanoma cells, highlighting its potential as an effective imaging probe for melanoma detection, as well as its potential as a therapeutic agent for melanoma treatment when labeled with a therapeutic radionuclide. As we anticipated, the strategy of reducing the ring size of the lactam bridge-cyclized α-MSH peptide resulted in improved tumor uptake and prolonged tumor retention. Compared to $^{111}$In-DOTA-GlyGlu-CycMSH with a 12-amino acid peptide ring, $^{111}$In-DOTA-Nle-CycMSH$_{hex}$ (FIG. 1) only had a 6-amino acid peptide ring. The tumor uptake value (19.39±2.72% ID/g) of $^{111}$In-DOTA-Nle-CycMSH$_{hex}$ was 1.86 times the tumor uptake value of $^{111}$In-DOTA-GlyGlu-CycMSH 2 h post-injection in B16/F1 melanoma-bearing C57 mice. $^{111}$In-DOTA-Nle-cMSH$_{hex}$ also exhibited prolonged tumor retention than $^{111}$In-DOTA-GlyGlu-CycMSH. At 24 h post-injection, 54.3% of $^{111}$In-DOTA-Nle-CycMSH$_{hex}$ activity at 2 h post-injection (10.53±1.11% ID/g) remained in the tumors (Table 1), whereas only 22.8% of the $^{111}$In-DOTA-GlyGlu-CycMSH radioactivity at 2 h post-injection (2.37±0.28% ID/g) remained inside the tumors. Urinary analysis demonstrated that the $^{111}$In-DOTA-Nle-CycMSH$_{hex}$ remained intact 2 h post-injection (FIG. 5C). It is likely that both high in vivo stability of $^{111}$In-DOTA-Nle-CycMSH$_{hex}$ and low MC1 receptor dissociation rate (15) contributed to the rapid high melanoma uptake (24.94±4.58% ID/g at 0.5 h post-injection) and prolonged tumor retention (10.53±1.11% ID/g at 24 h post-injection) of $^{111}$In-DOTA-Nle-CycMSH$_{hex}$ in B16/F1 melanoma-bearing C57 mice.

Figure 4:
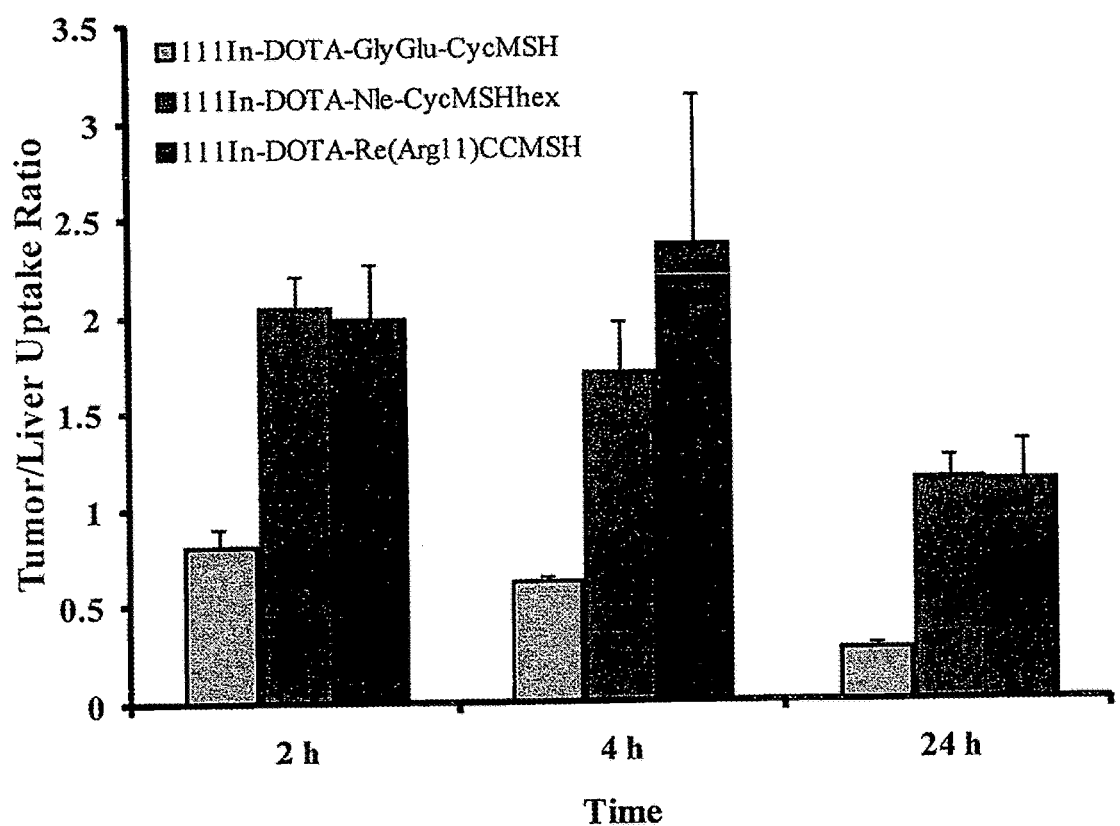
FIG. 4 shows tumor to kidney uptake ratios of $^{111}$In-DOTA-GlyGlu-CycMSH, $^{111}$In-DOTA-Nle-CycMSH$_{hex}$ and $^{111}$In-DOTA-Re(Arg$^{11}$)CCMSH at 2, 4 and 24 h post-injection. The tumor to kidney uptake ratios of $^{111}$In-DOTA-GlyGlu-CycMSH and $^{111}$In-DOTA-Re(Arg$^{11}$)CCMSH were calculated based on the results published in the references 19 and 17.

The reduction of the peptide ring size also decreased the non-specific kidney uptake of $^{111}$In-DOTA-Nle-CycMSH$_{hex}$ compared to $^{111}$In-DOTA-GlyGlu-CycMSH (19) at 2 and 4 h post-injection. The renal uptake values of $^{111}$In-DOTA-Nle-CycMSH$_{hex}$ were only 72.8% and 82.4% of the renal uptake values of $^{111}$In-DOTA-GlyGlu-CycMSH at 2 and 4 h post-injection, respectively. The renal uptake value of $^{111}$In-DOTA-Nle-CycMSH$_{hex}$ was further reduced with L-lysine co-injection by 30% at 2 h post-injection, demonstrating that the electrostatic interaction between $^{111}$In-DOTA-Nle-CycMSH$_{hex}$ and the kidney cells played an important role in the renal uptake of $^{111}$In-DOTA-Nle-CycMSH$_{hex}$. The synergistic effects of an increase of the tumor uptake and a decrease of the renal uptake dramatically improved the tumor to kidney uptake ratios of $^{111}$In-DOTA-Nle-CycMSH$_{hex}$ at all time points investigated in this study. Improved tumor uptake and decreased kidney uptake resulted in superior tumor/kidney uptake ratios of $^{111}$In-DOTA-Nle-CycMSH$_{hex}$ than those of $^{111}$In-DOTA-CycMSH-CycMSH at 2, 4 and 24 h post-injection. The tumor to kidney uptake ratios of $^{111}$In-DOTA-Nle-CycMSH$_{hex}$ were 2.55, 2.79 and 4.35 times the tumor to kidney uptake ratios of $^{111}$In-DOTA-GlyGlu-CycMSH at 2, 4 and 24 h post-injection, respectively (FIG. 4). $^{111}$In-DOTA-Nle-CycMSH$_{hex}$ remained intact in the urine 2 (FIG. 5C) whereas all of $^{111}$In-DOTA-CycMSH-CycMSH transformed into two polar metabolites in the urine 2 h post-injection (19), which might contribute to the decreased renal uptake of $^{111}$In-DOTA-Nle-CycMSH$_{hex}$.

Recently, $^{99m}$Tc-labeled lactam bridge-cyclized α-MSH peptides {[Ac-Nle$^4$,Asp$^5$,D-Phe$^7$,Lys $^{11}$(pz-$^{99m}$Tc(CO)$_3$)]α-MSH$_{4-11}$ and $^{99m}$Tc(CO)$_3$-pz-βAla-Nle-cyclo[Asp-His-D-Phe-Arg-Trp-Lys]-NH$_2$} have been reported for melanoma targeting (28, 29). $^{99m}$Tc(CO)$_3$-pz-βAla-Nle-cyclo[Asp-His-D-Phe-Arg-Trp-Lys]-NH$_2$ exhibited superior melanoma uptake (11.31±1.81% ID/g) to [Ac-Nle$^4$,Asp$^5$,D-Phe$^7$,Lys$^{11}$(pz-$^{99m}$Tc(CO)$_3$)]α-MSH$_{4-11}$ (4.24±0.94% ID/g) at 4 h post-injection in B16/F1 melanoma-bearing C57 mice. However, $^{99m}$Tc(CO)$_3$-pz-βAla-Nle-cyclo[Asp-His-D-Phe-Arg-Trp-Lys]-NH$_2$ displayed high accumulation and prolonged retention in both liver (22.86±1.17% ID/g) and kidneys (32.12±1.57% ID/g) at 4 h post-injection, which might limit its potential application in metastatic melanoma imaging. In this study, the tumor uptake of $^{111}$In-DOTA-Nle-CycMSH$_{hex}$ was 1.5 times the tumor uptake of $^{99m}$Tc(CO)$_3$-pz-βAla-Nle-cyclo[Asp-His-D-Phe-Arg-Trp-Lys]-NH$_2$ at 4 h post-injection, whereas the liver and renal uptake values of $^{111}$In-DOTA-Nle-CycMSH$_{hex}$ were only 7.5% and 31.1% of the $^{99m}$Tc(CO)$_3$-pz-βAla-Nle-cyclo[Asp-His-D-Phe-Arg-Trp-Lys]-NH$_2$ at 4 h post-injection. Dramatic increase of the tumor uptake and decrease of the liver and kidney uptakes of $^{111}$In-DOTA-Nle-CycMSH$_{hex}$ were likely due to the structural differences between $^{99m}$Tc(CO)$_3$-pz-βAla-Nle-cyclo[Asp-His-D-Phe-Arg-Trp-Lys]-NH$_2$ and $^{111}$In-DOTA-Nle-CycMSH$_{hex}$.

Currently, metal-cyclized $^{111}$In-DOTA-Re(Arg$^{11}$)CC-MSH showed the highest melanoma uptake among all reported $^{111}$In-labeled linear and cyclic α-MSH peptides (17). The tumor uptake values of $^{111}$In-DOTA-Re(Arg$^{11}$) CCMSH were 17.29±2.49, 17.41±5.63 and 8.19±1.63% ID/g at 2, 4 and 24 h post-injection, respectively (17). Remarkably, $^{111}$In-DOTA-Nle-CycMSH$_{hex}$ exhibited 1.12, 0.98 and 1.29 times the tumor uptake values of $^{111}$In-DOTA-Re(Arg$^{11}$)CCMSH at 2, 4 and 24 h post-injection, respectively. Meanwhile, $^{111}$In-DOTA-Nle-CycMSH$_{hex}$ showed slightly higher but similar renal uptake values to $^{111}$In-DOTA-Re(Arg$^{11}$)CCMSH at 2 and 4 h post-injection. $^{111}$In-DOTA-Nle-CycMSH$_{hex}$ exhibited comparable tumor to kidney ratios as $^{111}$In-DOTA-Re(Arg$^{11}$)CCMSH at 2 and 24 h post-injection despite that the tumor to kidney uptake ratio of $^{111}$In-DOTA-Nle-CycMSH$_{hex}$ was 28% less than that of $^{111}$In-DOTA-Re(Arg$^{11}$)CCMSH at 4 h post-injection. It was reported that a single-dose treatment of $^{212}$Pb-labeled DOTA-Re(Arg$^{11}$)CCMSH (200 uCi) resulted in 44% cures in B16/F1 melanoma-bearing mice (11). Accordingly, it would be likely that the treatment of $^{212}$Pb-labeled DOTA-Nle-CycMSH$_{hex}$ would yield similar quantitative therapeutic effect for melanoma in the future since $^{111}$In-DOTA-Nle-CycMSH$_{hex}$ displayed comparable tumor to kidney ratios as $^{111}$In-DOTA-Re(Arg$^{11}$)CCMSH at 2 and 24 h post-injection.

Conclusion

The ring size of the $^{111}$In-labeled lactam bridge-cyclized α-MSH peptide exhibited a profound effect on its melanoma targeting and pharmacokinetic properties. The reduction of the peptide ring size dramatically increased the melanoma uptake and decreased the renal uptake of $^{111}$In-DOTA-Nle-CycMSH$_{hex}$, providing a new insight into the design of novel radiolabeled lactam bridge-cyclized α-MSH peptide for melanoma imaging and treatment.

Further Examples

Materials and Methods
Chemicals and Reagents

Amino acids and resin were purchased from Advanced ChemTech Inc. (Louisville, Ky.) and Novabiochem (San Diego, Calif.). DOTA-tri-t-butyl ester was purchased from Macrocyclics Inc. (Richardson, Tex.) for peptide synthesis. $^{125}$I-Tyr$^2$-[Nle$^4$, D-Phe$^7$]-α-MSH {$^{125}$I-(Tyr$^2$)-NDP-MSH} was obtained from PerkinElmer, Inc. (Waltham, Mass.) for in vitro receptor binding assay. $^{111}$InCl$_3$ was purchased from Trace Life Sciences, Inc. (Dallas, Tex.) for radiolabeling. All other chemicals used in this study were purchased from Thermo Fischer Scientific (Waltham, Mass.) and used without further purification. B16/F1 murine melanoma cells were obtained from American Type Culture Collection (Manassas, Va.).

Peptide Synthesis

New DOTA-GGNle-CycMSH$_{hex}$, DOTA-GENle-CycMSH$_{hex}$ and DOTA-NleGE-CycMSH$_{hex}$ peptides were synthesized using standard fluorenylmethyloxycarbonyl (Fmoc) chemistry according to the inventors' published procedure (19, second set of references) with modifications. Briefly, linear peptide backbones of (tBu)$_3$DOTA-Gly-Gly-Nle-Asp(O-2-PhiPr)-His(Trt)-DPhe-Arg(Pbf)-Trp(Boc)-Lys(Dde), (tBu)$_3$DOTA-Gly-Glu(OtBu)-Nle-Asp(O-2-PhiPr)-His(Trt)-DPhe-Arg(Pbf)-Trp(Boc)-Lys(Dde) and (tBu)$_3$DOTA-Nle-Gly-Glu(OtBu)-Asp(O-2-PhiPr)-His(Trt)-DPhe-Arg(Pbf)-Trp(Boc)-Lys(Dde) were synthesized on Sieber Amide resin by an Advanced ChemTech multiple-peptide synthesizer (Louisville, Ky.). Seventy micromoles of resin, 210 μmol of each Fmoc-protected amino acid and 210 μmol of (tBu)$_3$DOTA were used for the synthesis. The protecting group of Dde was removed by 2% hydrazine for peptide cyclization. The protecting group of 2-phenylisopropyl was removed and the protected peptide was cleaved from the resin treating with a mixture of 2.5% of trifluoroacetic acid (TFA) and 5% of triisopropylsilane. After the precipitation with ice-cold ether and characterization by liquid chromatography-mass spectroscopy (LC-MS), each protected peptide was dissolved in H$_2$O/CH$_3$CN (50:50) and lyophilized to remove the reagents. Then, each protected peptide was further cyclized by coupling the carboxylic group from the Asp with the epsilon amino group from the Lys. The cyclization reaction was achieved by an overnight reaction in dimethylformamide (DMF) using benzotriazole-1-yl-oxy-tris-pyrrolidino-phosphonium-hexafluorophosphate (PyBOP) as a coupling agent in the presence of N,N-diisopropylethylamine (DIEA). After the characterization by LC-MS, each cyclized protected peptide was dissolved in H$_2$O/CH$_3$CN (50:50) and lyophilized to remove the reagents. The protecting groups were totally removed by treating with a mixture of trifluoroacetic acid (TFA), thioanisole, phenol, water, ethanedithiol and triisopropylsilane (87.5:2.5:2.5:2.5:2.5:2.5) for 2 h at room temperature (25° C.). Each peptide was precipitated and washed with ice-cold ether four times, purified by reverse phase-high performance liquid chromatography (RP-HPLC) and characterized by LC-MS.

In Vitro Receptor Binding Assay

The receptor binding affinities (IC$_{50}$ values) of DOTA-GGNle-CycMSH$_{hex}$, DOTA-GENle-CycMSH$_{hex}$ and DOTA-NleGE-CycMSH$_{hex}$ were determined by in vitro competitive binding assay according to the published procedure (19) with modifications. B16/F1 cells in 24-well cell culture plates (5×10$^5$ cells/well) were incubated at room temperature (25° C.) for 2 h with approximately 60,000 cpm of $^{125}$I-Tyr$^2$-NDP-MSH in the presence of 10$^{-12}$ to 10$^{-5}$ M of each peptide in 0.3 mL of binding medium {Dulbecco's Modified Eagle's Medium with 25 mM N-(2-hydroxyethyl)-piperazine-N'-(2-ethanesulfonic acid), pH 7.4, 0.2% bovine serum albumin (BSA), 0.3 mM 1,10-phenathroline}. The medium was aspirated after the incubation. The cells were rinsed twice with 0.5 mL of ice-cold pH 7.4, 0.2% BSA/0.01 M phosphate buffered saline (PBS) and lysed in 0.5 mL of 1 N NaOH for 5 minutes. The activities associated with cells were measured in a Wallac 1480 automated gamma counter (PerkinElmer, Waltham, Mass.). The IC$_{50}$ value of each peptide was calculated using Prism software (GraphPad Software, La Jolla, Calif.).

Peptide Radiolabeling with $^{111}$In

Since DOTA-NleGE-CycMSH$_{hex}$ exhibited at least 78-fold lower receptor binding affinity than DOTA-GGNle-CycMSH$_{hex}$ and DOTA-GENle-CycMSH$_{hex}$, we only further evaluated DOTA-GGNle-CycMSH$_{hex}$ and DOTA-GENle-CycMSH$_{hex}$. $^{111}$In-DOTA-GGNle-CycMSH$_{hex}$ and $^{111}$In-DOTA-GENle-CycMSH$_{hex}$ were prepared in a 0.5 M NH$_4$OAc-buffered solution at pH 4.5 according to our published procedure (19). Briefly, 50 μL of $^{111}$InCl$_3$ (37-74 MBq in 0.05 M HCl aqueous solution), 10 μL of 1 mg/mL peptide aqueous solution and 400 μL of 0.5 M NH$_4$OAc (pH 4.5) were added into a reaction vial and incubated at 75° C. for 45 mins. After the incubation, 10 μL of 0.5% EDTA (ethylenediaminetetraacetic acid) aqueous solution was added into the reaction vial to scavenge potential unbound $^{111}$In$^{3+}$ ions. The radiolabeled complexes were purified to single species by Waters RP-HPLC (Milford, Mass.) on a Grace Vydac C-18 reverse phase analytical column (Deerfield, Ill.) using the following gradient at a 1 mL/min flowrate. The mobile phase consisted of solvent A (20 mM HCl aqueous solution) and solvent B (100% $CH_3CN$). The gradient was initiated and kept at 82:18 A/B for 3 mins followed by a linear gradient of 82:18 A/B to 72:28 A/B over 20 mins. Then, the gradient was changed from 72:28 A/B to 10:90 A/B over 3 mins followed by an additional 5 mins at 10:90 A/B. Thereafter, the gradient was changed from 10:90 AB to 82:18 AB over 3 mins. Each purified peptide sample was purged with $N_2$ gas for 20 mins to remove the acetonitrile. The pH of the final solution was adjusted to 7.4 with 0.1 N NaOH and sterile saline for animal studies. In vitro serum stability of $^{111}$In-DOTA-GGNle-CycMSH$_{hex}$ and $^{111}$In-DOTA-GENle-CycMSH$_{hex}$ were determined by incubation in mouse serum at 37° C. for 24 h and monitored for degradation by RP-HPLC.

Biodistribution Studies

All animal studies were conducted in compliance with Institutional Animal Care and Use Committee approval. The pharmacokinetics of $^{111}$In-DOTA-GGNle-CycMSH$_{hex}$ and $^{111}$In-DOTA-GENle-CycMSH$_{hex}$ were determined in B16/F1 melanoma-bearing C57 female mice (Harlan, Indianapolis, Ind.). The C57 mice were subcutaneously inoculated with $1\times10^6$ B16/F1 cells on the right flank for each mouse to generate B16/F1 melanomas. Ten days post inoculation, the tumor weights reached approximately 0.2 g. Each melanoma-bearing mouse was injected with 0.037 MBq of $^{111}$In-DOTA-GGNle-CycMSH$_{hex}$ or $^{111}$In-DOTA-GENle-CycMSH$_{hex}$ via the tail vein. Groups of 5 mice were sacrificed at 0.5, 2, 4 and 24 h post-injection, and tumors and organs of interest were harvested, weighed and counted. Blood values were taken as 6.5% of the whole-body weight. The specificities of the tumor uptake of $^{111}$In-DOTA-GGNle-CycMSH$_{hex}$ and $^{111}$In-DOTA-GENle-CycMSH$_{hex}$ were determined by co-injecting 10 μg (6.07 nmol) of unlabeled NDP-MSH which is a linear α-MSH peptide analogue with picomolar MC1 receptor binding affinity.

Melanoma Imaging

Since $^{111}$In-DOTA-GGNle-CycMSH$_{hex}$ displayed more favorable tumor targeting and pharmacokinetic properties than $^{111}$In-DOTA-GENle-CycMSH$_{hex}$, we only further evaluated the melanoma imaging property of $^{111}$In-DOTA-GGNle-CycMSH$_{hex}$. One B16/F1 melanoma-bearing C57 mouse (10 days post the cell inoculation) was injected with 37.0 MBq of $^{111}$In-DOTA-GGNle-CycMSH$_{hex}$ via the tail vein. The mouse was sacrificed for small animal SPECT/CT (Nano-SPECT/CT®, Bioscan) imaging at 2 h post-injection. The CT imaging was immediately followed by the whole-body SPECT imaging. The SPECT scans of 24 projections were acquired. Reconstructed SPECT and CT data were visualized and co-registered using InVivoScope (Bioscan, Washington D.C.).

Metabolites of $^{111}$In-DOTA-GGNle-CycMSH$_{hex}$ in Melanoma and Urine

Both melanoma and urine were collected from the mouse used for SPECT/CT imaging to analyze the metabolites of $^{111}$In-DOTA-GGNle-CycMSH$_{hex}$ in melanoma and urine. The tumor was homogenized by a VWR homogenizer for 5 mins. Equal volume of ethanol was added into the tumor sample. The tumor sample was vortexed and then centrifuged at 16,000 g for 5 mins. The supernatant was transferred into a glass test tube and purged with $N_2$ gas for 20 mins to remove the ethanol. Aliquots of the supernatant were injected into HPLC. The urinary sample was directly centrifuged at 16,000 g for 5 mins prior to the HPLC analysis. Thereafter, aliquots of the urine were injected into HPLC. The HPLC gradient described above was used for the analyses of metabolites.

Statistical Analysis

Statistical analysis was performed using the Student's t-test for unpaired data. A 95% confidence level was chosen to determine the significant difference in tumor and renal uptakes between $^{111}$In-DOTA-GGNle-CycMSH$_{hex}$ and $^{111}$In-DOTA-GENle-CycMSH$_{hex}$, as well as the significant difference in tumor and renal uptakes between $^{111}$In-DOTA-GGNle-CycMSH$_{hex}$ or $^{111}$In-DOTA-GENle-CycMSH$_{hex}$ with/without NDP-MSH co-injection. The differences at the 95% confidence level ($p<0.05$) were considered significant.

Results

Figure 6:
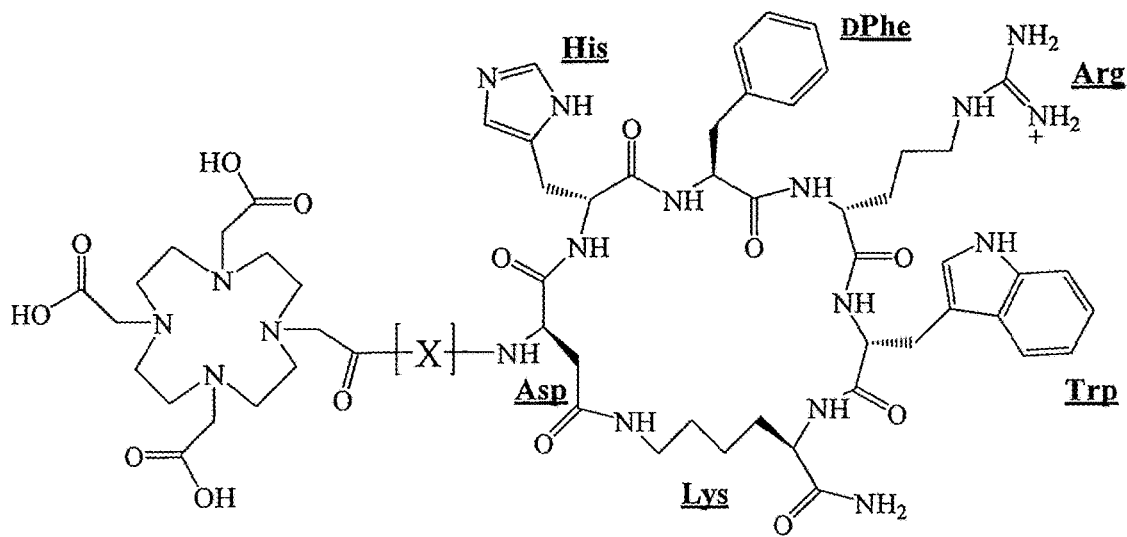
FIG. 6 shows representative compounds according to the present invention with certain amino acid and/or peptide linkers.
Figure 7:
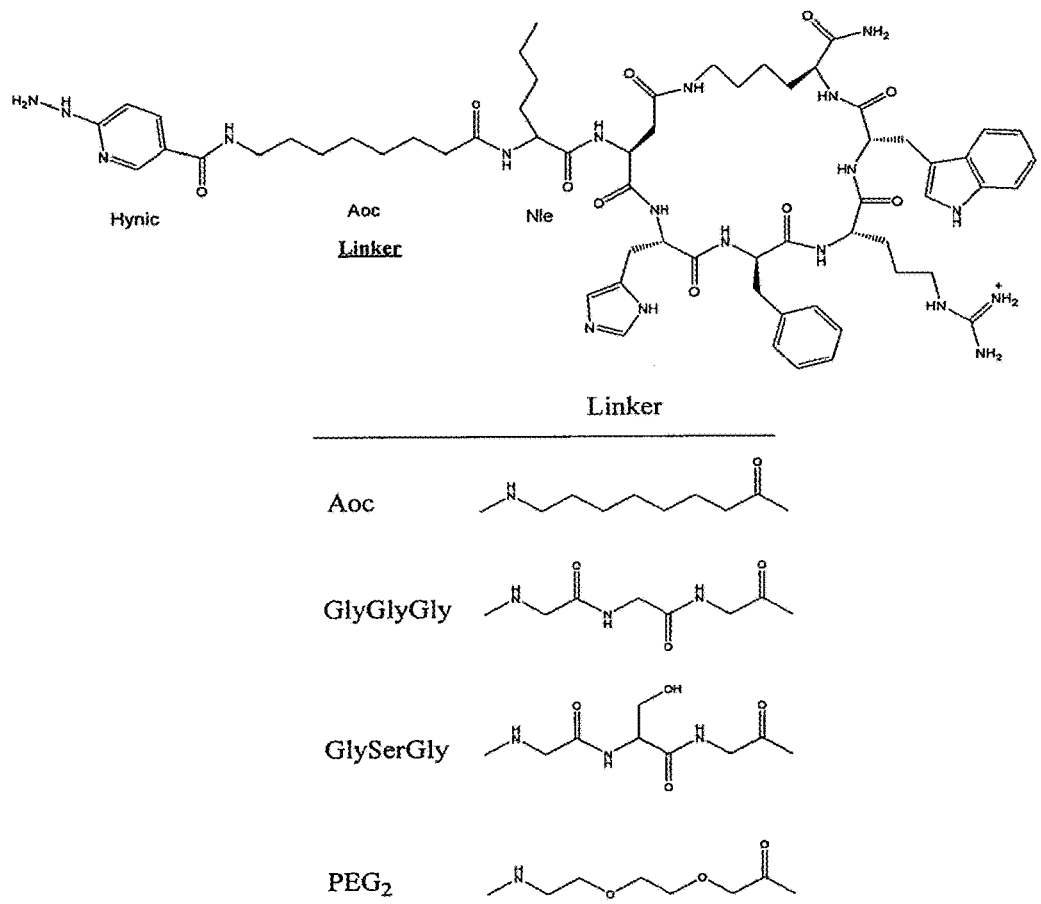
FIG. 7 shows representative compounds according to the present invention with representative linkers.
Figure 7:
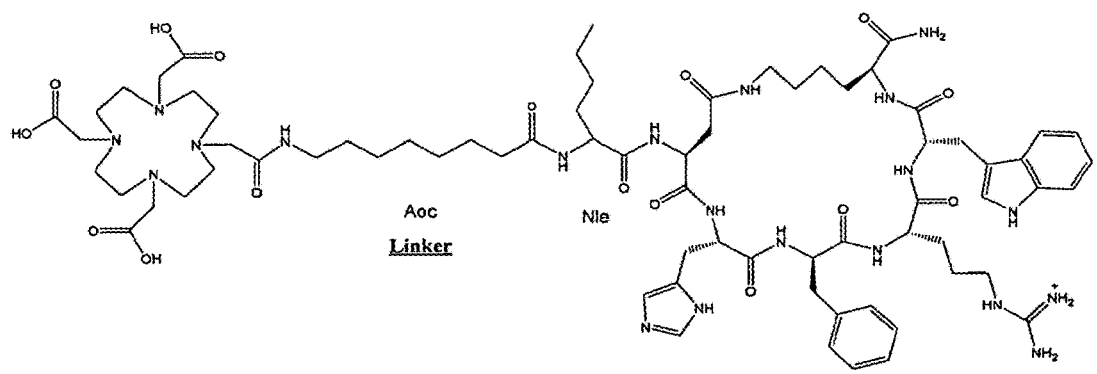
Figure 8:
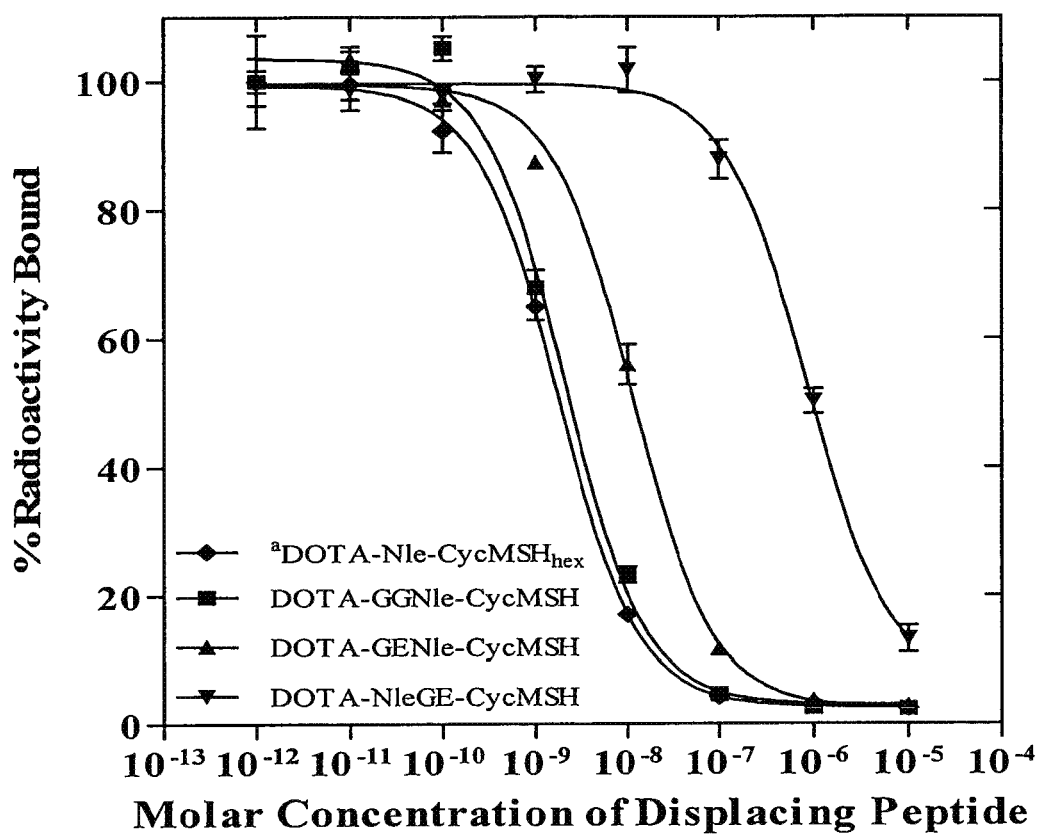
FIG. 8 shows the in vitro competitive binding curves of DOTA-Nle-CycMSH$_{hex}$, DOTA-GGNle-CycMSH$_{hex}$, DOTA-GENle-CycMSH$_{hex}$ and DOTA-NleGE-CycMSH$_{hex}$ in B16/F1 melanoma cells. The IC$_{50}$ values of DOTA-Nle-CycMSH$_{hex}$, DOTA-GGNle-CycMSH$_{hex}$, DOTA-GENle-CycMSH$_{hex}$ and DOTA-NleGE-CycMSH$_{hex}$ were 1.8, 2.1, 11.5 and 873.4 nM respectively. "The Data of DOTA-Nle-CycMSH$_{hex}$ was cited from reference 19 for comparison.

Three novel α-MSH peptides, DOTA-GGNle-CycMSH$_{hex}$, DOTA-GENle-CycMSH$_{hex}$ and DOTA-NleGE-CycMSH$_{hex}$ were synthesized and purified by HPLC. All three peptides displayed greater than 95% purity after HPLC purification. The schematic structures of the peptides are shown in FIG. 6. The identities of the peptides were confirmed by electrospray ionization mass spectrometry. The calculated and found molecular weights of the peptides are presented in Table 1A. The receptor binding affinities of the peptides were determined in B16/F1 melanoma cells. The $IC_{50}$ values of DOTA-GGNle-CycMSH$_{hex}$ DOTA-GENle-CycMSH$_{hex}$ and DOTA-NleGE-CycMSH$_{hex}$ were 2.1, 11.5 and 873.4 nM in B16/F1 cells, respectively (Table 1 and FIG. 8).

Only DOTA-GGNle-CycMSH$_{hex}$ and DOTA-GENle-CycMSH$_{hex}$ displayed low nanomolar MC1 receptor binding affinities. Hence, we only further evaluated DOTA-GGNle-CycMSH$_{hex}$ and DOTA-GENle-CycMSH$_{hex}$. DOTA-GGNle-CycMSH$_{hex}$ and DOTA-GENle-CycMSH$_{hex}$ were readily labeled with $^{111}$In in 0.5 M ammonium acetate solution at pH 4.5 with greater than 95% radiolabeling yield. Each $^{111}$In-labeled peptide was completely separated from its excess non-labeled peptide by RP-HPLC. The retention times of the peptides and their $^{111}$In-labeled conjugates are showed in Table 1A. The retention times of $^{111}$In-DOTA-GGNle-CycMSH$_{hex}$ and $^{111}$In-DOTA-GENle-CycMSH$_{hex}$ were 17.7 and 21.7 min, respectively. $^{111}$In-DOTA-GGNle-CycMSH$_{hex}$ and $^{111}$In-DOTA-GENle-CycMSH$_{hex}$ showed greater than 98% radiochemical purities after HPLC purification, and were stable in mouse serum at 37° C. for 24 h. Only intact $^{111}$In-labeled conjugates were detected by RP-HPLC after 24 h of incubation in mouse serum.

The inventors further evaluated the melanoma targeting and pharmacokinetic properties of $^{111}$In-DOTA-GGNle-CycMSH$_{hex}$ and $^{111}$In-DOTA-GENle-CycMSH$_{hex}$ in B16/F1 melanoma-bearing C57 mice. The biodistribution results of $^{111}$In-DOTA-GGNle-CycMSH$_{hex}$ and $^{111}$In-DOTA-GENle-CycMSH$_{hex}$ are shown in Table 2A. $^{111}$In-DOTA-GGNle-CycMSH$_{hex}$ exhibited rapid high melanoma uptake and prolonged tumor retention. The tumor uptake value of $^{111}$In-DOTA-GGNle-CycMSH$_{hex}$ was 18.39±2.22% ID/g at 0.5 h post-injection. The tumor uptake reached its peak value of 19.05±5.04% ID/g at 2 h post-injection. $^{111}$In-DOTA-GGNle-CycMSH$_{hex}$ displayed similar high tumor uptake (18.6±3.56% ID/g) at 4 h post-injection. Even at 24 h post-injection, there was 6.77±0.84% ID/g of $^{111}$In-DOTA-GGNle-CycMSH$_{hex}$ activity remained in the tumor. Approximately 98% of the tumor uptake of $^{111}$In-DOTA-GGNle-CycMSH$_{hex}$ was blocked by 10 μg (6.07 nmol) of non-radiolabeled NDP-MSH ($p<0.05$), demonstrating that the tumor uptake was specific and MC1 receptor-mediated. Whole-body clearance of $^{111}$In-DOTA-GGNle-CycMSH$_{hex}$ was rapid, with approximately 88.4% of the injected radioactivity cleared through the urinary system by 2 h post-injection (Table 2A). Normal organ uptakes of $^{111}$In-DOTA-GGNle-CycMSH$_{hex}$ were low (<1.31% ID/g) except for the kidneys 2, 4 and 24 h post-injection. The liver uptake of $^{111}$In-DOTA-GGNle-CycMSH$_{hex}$ was less than 0.61% ID/g at 2 h post-injection (Table 2A). The kidney uptake value was 15.19±2.75% ID/g at 0.5 h post-injection, and decreased to 6.84±0.92% ID/g at 2 h post-injection (Table 2A). Co-injection of NDP-MSH didn't significantly reduce the renal uptake of the $^{111}$In-DOTA-GGNle-CycMSH$_{hex}$ activity at 2 h post-injection, indicating that the renal uptake was not MC1 receptor-mediated. High tumor uptake and prolonged tumor retention coupled with rapid whole-body clearance resulted in high tumor/blood and high tumor/normal organ uptake ratios that were achieved as early as 0.5 h post-injection (Table 2A). The tumor/liver uptake ratios of $^{111}$In-DOTA-GGNle-CycMSH$_{hex}$ were 33.42 and 31.0 at 2 and 4 h post-injection, whereas the tumor/kidney uptake ratios of $^{111}$In-DOTA-GGNle-CycMSH$_{hex}$ were 2.79 and 2.73 at 2 and 4 h post-injection.

$^{111}$In-DOTA-GENle-CycMSH$_{hex}$ showed lower tumor uptake values than $^{111}$In-DOTA-GGNle-CycMSH$_{hex}$ at 0.5, 2 and 4 h post-injection. The tumor uptake values of $^{111}$In-DOTA-GGNle-CycMSH$_{hex}$ were 2, 2.5 and 3 times the tumor uptake values of $^{111}$In-DOTA-GENle-CycMSH$_{hex}$ at 0.5, 2 and 4 h post-injection, respectively (Table 2A). Co-injection of non-radioactive NDP-MSH blocked 95.6% of the tumor uptake at 2 h post-injection (p<0.05), indicating that the tumor uptake of $^{111}$In-DOTA-GENle-CycMSH$_{hex}$ was MC1 receptor-specific. Despite the similar renal uptake of $^{111}$In-DOTA-GENle-CycMSH$_{hex\ as}$ $^{111}$In-DOTA-GGNle-CycMSH$_{hex}$ at 2, 4 and 24 h post-injection, $^{111}$In-DOTA-GENle-CycMSH$_{hex}$ showed 40% lower renal uptake than $^{111}$In-DOTA-GGNle-CycMSH$_{hex}$ at 0.5 h post-injection (p<0.05). The kidney uptake of $^{111}$In-DOTA-GENle-CycMSH$_{hex}$ was as low as 9.06±2.20% ID/g at 0.5 h post-injection and decreased to 5.54±0.63% ID/g at 2 h post-injection.

We further evaluated the melanoma imaging properties of $^{111}$In-DOTA-GGNle-CycMSH$_{hex}$ since $^{111}$In-DOTA-GGNle-CycMSH$_{hex}$ showed more favorable biodistribution properties than $^{111}$In-DOTA-GENle-CycMSH$_{hex}$. The whole-body SPECT/CT images are presented in FIG. 9. Flank melanoma tumors were clearly visualized by SPECT/CT using $^{111}$In-DOTA-GGNle-CycMSH$_{hex}$ as an imaging probe. The whole-body images showed high tumor to normal organ uptake ratios except for the kidneys, which was consistent with the biodistribution results. Melanoma and urinary metabolites of $^{111}$In-DOTA-GGNle-CycMSH$_{hex}$ were analyzed by RP-HPLC 2 h post-injection. FIG. 10 illustrates both the HPLC profiles of melanoma and urine samples. In-DOTA-GGNle-CycMSH$_{hex}$ remained intact in the both tumor and urine 2 h post-injection (FIG. 10).

Discussion

The present inventors have been interested in developing lactam bridge-cyclized α-MSH peptides to target the MC1 receptors for melanoma detection (15-19). Unique lactam bridge-cyclization makes the cyclic α-MSH peptides resistant to proteolytic degradations in vivo, as well as provides the flexibility for fine structural modification (15, 17, 19). Recently, we have identified $^{111}$In-DOTA-Nle-CycMSH$_{hex}$ with a 6-amino acid ring targeting the MC1 receptors for melanoma imaging (19). Among these reported $^{111}$In-labeled lactam bridge-cyclized α-MSH peptides (15, 17, 19), $^{111}$In-DOTA-Nle-CycMSH$_{hex}$ displayed the highest melanoma uptake values (24.94±4.58% ID/g at 0.5 h post-injection and 19.39±1.65% ID/g at 2 h post-injection) in B16/F1 melanoma-bearing mice (19). The reduction of the ring size improved the tumor uptake and reduced the renal uptake of $^{111}$In-DOTA-Nle-CycMSH$_{hex}$, providing a new insight into the design of novel lactam bridge-cyclized α-MSH peptides for melanoma targeting.

Hydrocarbon, amino acid and PEG linkers have been used to optimize the receptor binding affinities, as well as modifying the pharmacokinetic properties of radiolabeled bombesin (21-25), RGD (26-29) and α-MSH peptides (15, 16). For instance, Volkert and colleagues reported that the hydrocarbon linkers ranging from 5-carbon to 8-carbon between the DOTA and bombesin peptide resulted in 0.6-1.7 nM receptor binding affinities for the DOTA-conjugated bombesin peptides. Either shorter or longer hydrocarbon linkers dramatically reduce the receptor binding affinity by 100-fold (21). Rogers and colleagues reported the profound effects of amino acid linkers (-GlyGlyGly-, -GlySerGly-, -GlySerSer- and -GlyGluGly-) between the DOTA and bombesin peptide on tumor and normal organ uptakes of the radiolabeled peptides (25). $^{64}$Cu-labeled DOTA-conjugated bombesin peptide with the -GlyGlyGly- linker displayed the higher PC-3 tumor uptake, whereas the -GlySerGly- linker resulted in lower renal uptake (25). Recently, Liu and colleagues reported the improvement in tumor uptakes and pharmacokinetics of $^{64}$Cu- and $^{99m}$Tc-labeled cyclic RGD peptides using the -GlyGlyGly- and PEG$_4$ linkers (26-29). We also demonstrated that the introduction of a negatively-charged -GlyGlu- linker enhanced the melanoma uptake and reduced the renal uptake of $^{111}$In-DOTA-GlyGlu-CycMSH compared to $^{111}$In-DOTA-CycMSH (15). Hence, we evaluated the effects of -GlyGly- and -GlyGlu- linkers on melanoma targeting and pharmacokinetic properties of $^{111}$In-DOTA-[X]-CycMSH$_{hex}$ peptide constructs in this study.

DOTA-Nle-CycMSH$_{hex}$ displayed 1.8 nM MC1 receptor binding affinity in B16/F1 melanoma cells in our previous report (19). The MC1 receptor binding sequence of His-dPhe-Arg-Trp was directly cyclized by an Asp-Lys lactam bridge to generate the CycMSH$_{hex}$ moiety. The radiometal chelator DOTA was conjugated to the CycMSH$_{hex}$ moiety via a Nle to form DOTA-Nle-CycMSH$_{hex}$ peptide. Based on the unique structure of DOTA-Nle-CycMSH$_{hex}$, we initially introduced the amino acid linker (-GlyGlu-) between the DOTA and Nle or between the Nle and CycMSH$_{hex}$ moiety to determine which position was suitable for an amino acid linker. We found that the moiety of Nle-CycMSH$_{hex}$ was critical for maintaining the low nanomolar MC1 receptor binding affinity of the peptide. The introduction of the -GlyGlu- linker between the Nle and CycMSH$_{hex}$ moiety dramatically reduced the MC1 receptor binding affinity to 873.4 nM, whereas the introduction of the -GlyGlu- linker between the DOTA and Nle only decreased the MC1 receptor binding affinity to 11.5 nM. Interestingly, the -GlyGly- linker between the DOTA and Nle maintained the MC1 receptor binding affinity as 2.1 nM, further indicating the the moiety of Nle-CycMSH$_{hex}$ played a crucial role in maintaining the low nanomolar MC1 receptor binding affinity of the peptide. The difference in MC1 receptor binding affinity between DOTA-GGNle-CycMSH$_{hex}$ and DOTA-GENle-CycMSH$_{hex}$ (2.1 nM vs. 11.5 nM) was also observed in the melanoma uptakes of $^{111}$In-DOTA-GGNle-CycMSH$_{hex}$ and $^{111}$In-DOTA-GENle-CycMSH$_{hex}$ in B16/F1 melanoma-bearing C57 mice. The tumor uptake values of $^{111}$In-DOTA-GGNle-CycMSH$_{hex}$ were 2, 2.5 and 3 times the tumor uptake values of $^{111}$In-DOTA-GENle-CycMSH$_{hex}$ at 0.5, 2 and 4 h post-injection, respectively (Table 2A). In our previous report, the introduction of a negatively-charged -GlyGlu- linker resulted in 44% lower renal uptake of $^{111}$In-DOTA-GlyGlu-CycMSH at 4 h post-injection compared to $^{111}$In-DOTA-CycMSH (15). In this study, $^{111}$In-DOTA-GENle-CycMSH$_{hex}$ showed 40% lower renal uptake (p<0.05) than $^{111}$In-DOTA-GGNle-CycMSH$_{hex}$ at 0.5 h post-injection (Table 2A).

Figure 11:
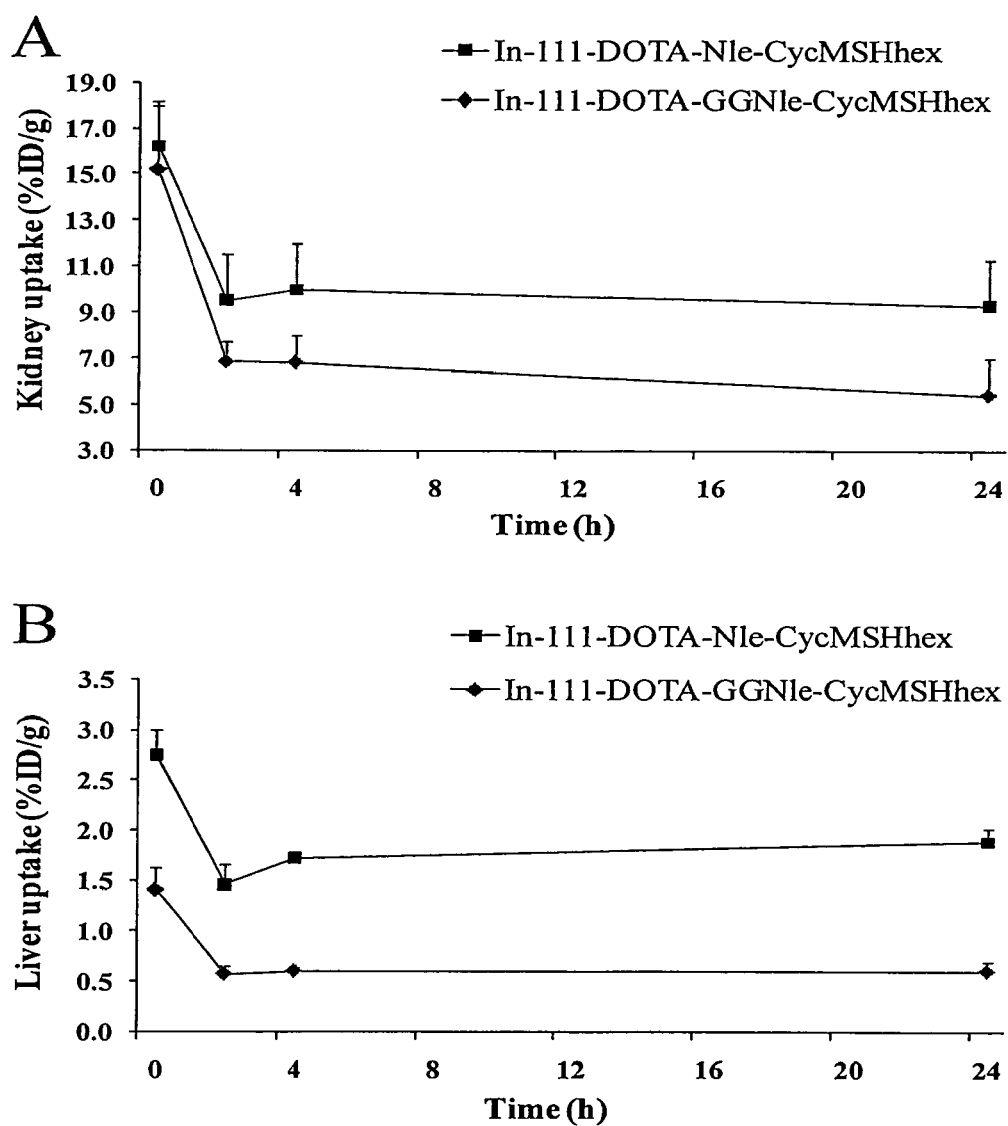
FIG. 11 shows the kidney (A) and liver (B) uptake values of $^{111}$In-DOTA-Nle-CycMSH$_{hex}$ (■) and $^{111}$In-DOTA-GGNle-CycMSH$_{hex}$ (♦). The Data of $^{111}$In-DOTA-Nle-CycMSH$_{hex}$ was cited from reference 19 (second reference set) for comparison.
Figure 12:
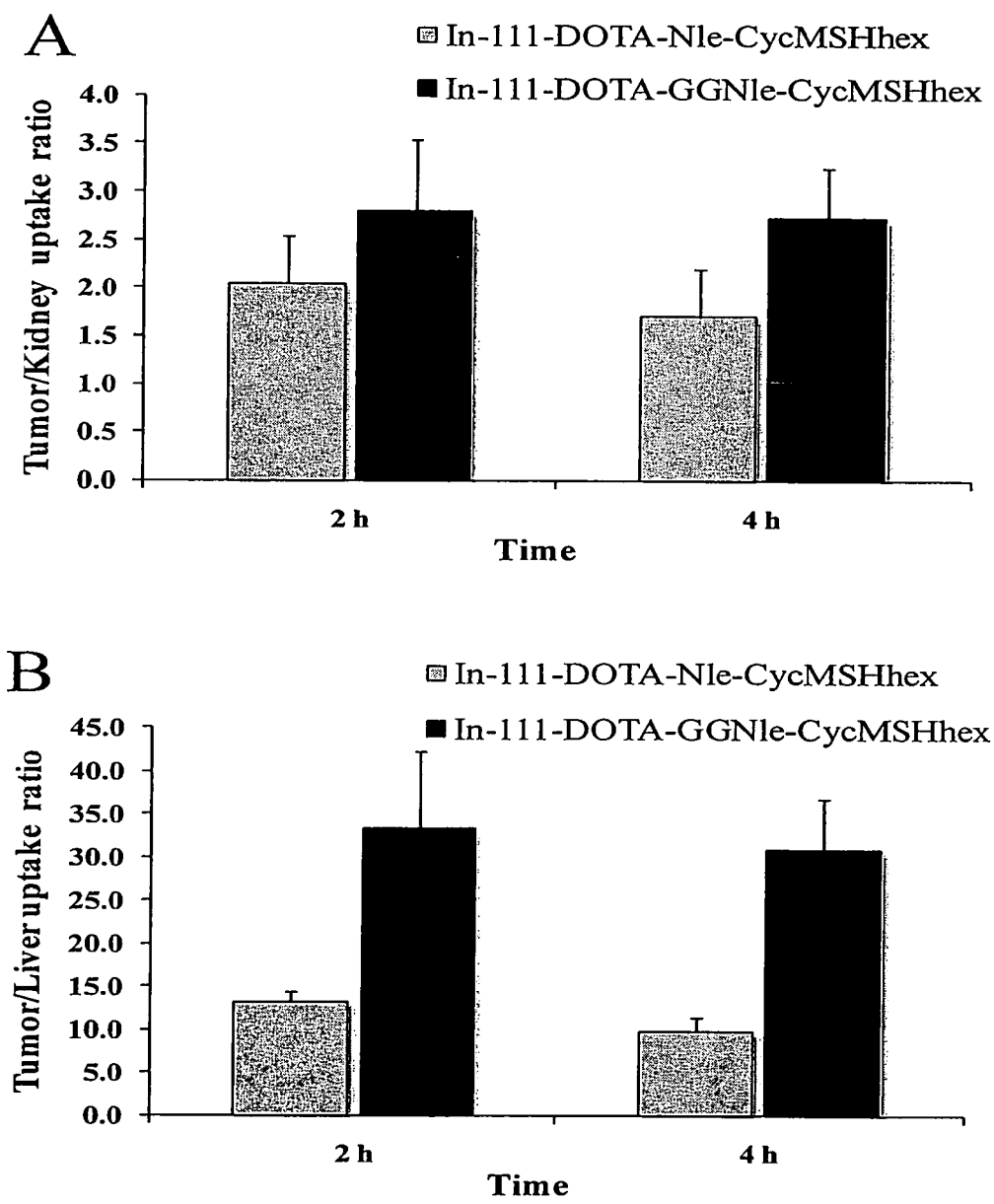
FIG. 12 shows the tumor/kidney (A) and tumor/liver (B) ratios of $^{111}$In-DOTA-Nle-CycMSH$_{hex}$ (▨) and $^{111}$In-DOTA-GGNle-CycMSH$_{hex}$ (■) at 2 and 4 h post-injection. The Data of $^{111}$In-DOTA-Nle-CycMSH$_{hex}$ was cited from reference 19 for comparison.

At the present time, the lactam bridge-cyclized $^{111}$In-DOTA-Nle-CycMSH$_{hex}$ and the metal-cyclized $^{111}$In-DOTA-Re(Arg[11])CCMSH displayed the highest comparable melanoma uptakes among all reported $^{111}$In-labeled linear and cyclic α-MSH peptides (13, 19). The melanoma uptake values were 17.29±2.49 and 17.41±5.63% ID/g at 2 and 4 h post-injection for $^{111}$In-DOTA-Re(Arg[11])CCMSH (13), whereas the melanoma uptake values were 19.39±1.65 and 17.01±2.54% ID/g at 2 and 4 h post-injection for $^{111}$In-DOTA-Nle-CycMSH$_{hex}$ (19). Meanwhile, $^{111}$In-DOTA-Nle-CycMSH$_{hex}$ showed similar tumor/kidney uptake ratios as $^{111}$In-DOTA-Re(Arg[11])CCMSH at 2 and 24 h post-injection (19). In this study, the introduction of the -GlyGly- linker maintained high melanoma uptakes of $^{111}$In-DOTA-GGNle-CycMSH$_{hex}$ (19.05±5.04 and 18.6±3.56% ID/g at 2 and 4 h post-injection, respectively) compared to $^{111}$In-DOTA-Nle-CycMSH$_{hex}$. Interestingly, the introduction of -GlyGly- linker reduced the liver and renal uptakes of $^{111}$In-DOTA-GGNle-CycMSH$_{hex}$. $^{111}$In-DOTA-GGNle-CycMSH$_{hex}$ exhibited 61, 65 and 68% less liver uptake values than $^{111}$In-DOTA-Nle-CycMSH$_{hex}$ (FIG. 11), and 28, 32 and 42% less renal uptake values than $^{111}$In-DOTA-Nle-CycMSH$_{hex}$ at 2, 4 and 24 h post-injection (FIG. 11), respectively. The maintained high melanoma uptakes coupled with the decreased liver and renal uptakes resulted in enhanced tumor/liver and tumor/kidney uptake ratios for $^{111}$In-DOTA-GGNle-CycMSH$_{hex}$ compared to $^{111}$In-DOTA-Nle-CycMSH$_{hex}$ at 2 and 4 h post-injection (FIG. 12). The tumor/liver uptake ratios of $^{111}$In-DOTA-GGNle-CycMSH$_{hex}$ were 2.52 and 3.13 times the tumor/liver uptake ratios of $^{111}$In-DOTA-Nle-CycMSH$_{hex}$ at 2 and 4 h post-injection, whereas the tumor/kidney uptake ratios of $^{111}$In-DOTA-GGNle-CycMSH$_{hex}$ were 1.37 and 1.61 times the tumor/kidney uptake ratios of $^{111}$In-DOTA-Nle-CycMSH$_{hex}$ at 2 and 4 h post-injection.

Figure 9:
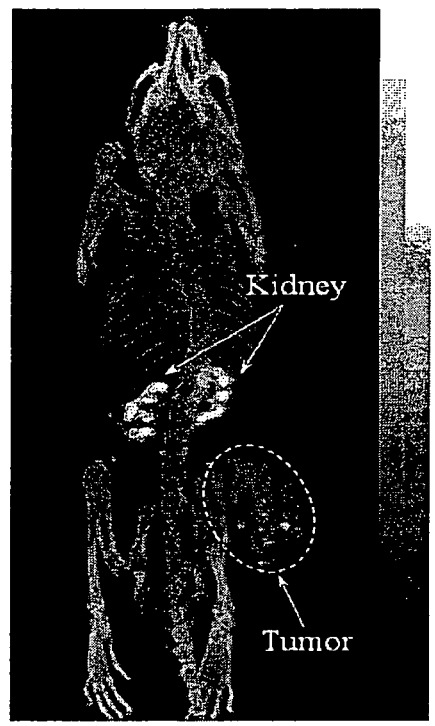
FIG. 9 shows representative whole-body SPECT/CT images of a B16/F1 melanoma-bearing mouse (14 days post cell inoculation) at 2 h post-injection of 37.0 MBq of $^{111}$In-DOTA-GGNle-CycMSH$_{hex}$.
Figure 10:
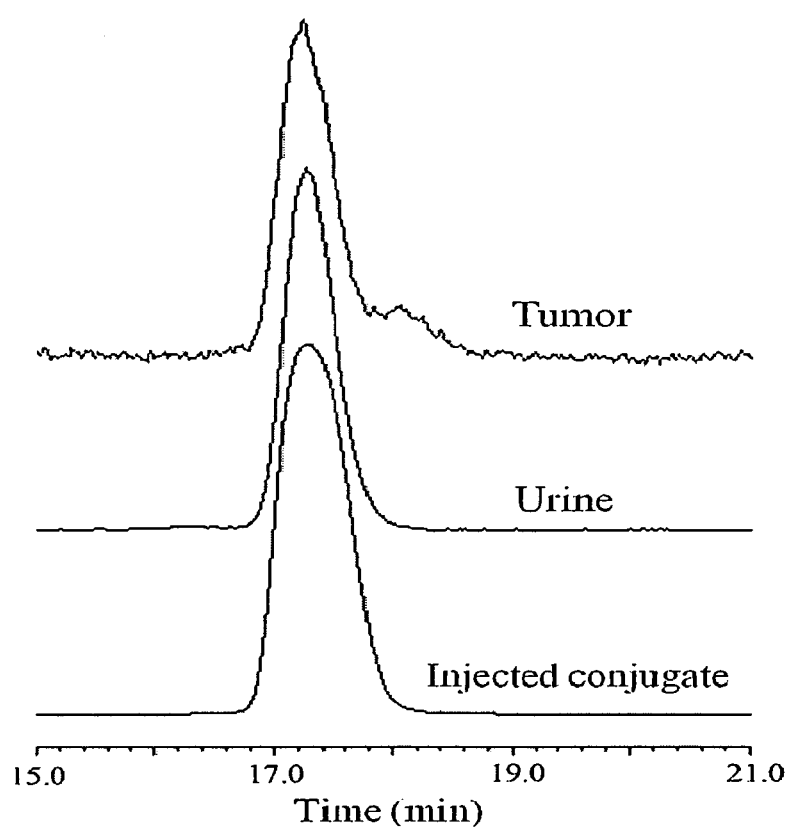
FIG. 10 shows the radioactive HPLC profiles of $^{111}$In-DOTA-GGNle-CycMSH$_{hex}$ (injected conjugate) and its metabolites in urine and tumor at 2 h post-injection.

As showed in FIG. 9, the enhanced tumor/liver and tumor/kidney uptake ratios of $^{111}$In-DOTA-GGNle-CycMSH$_{hex}$ generated high tumor imaging contrast to the background. The flank melanoma lesions were clearly visualized by SPECT/CT using $^{111}$In-DOTA-GGNle-CycMSH$_{hex}$ as an imaging probe, highlighting its potential as an effective imaging agent for melanoma detection. Furthermore, from the therapeutic point of view, the enhanced tumor/liver and tumor/kidney uptake ratios of $^{111}$In-DOTA-GGNle-CycMSH$_{hex}$ would decrease the absorbed doses to the liver and kidneys when using the therapeutic radionuclide-labeled DOTA-GGNle-CycMSH$_{hex}$ for melanoma treatment. In other words, the improvement of tumor/liver and tumor/kidney uptake ratios would potentially increase the absorbed dose to the tumor while keeping the liver and kidneys safe when treating the melanoma with the therapeutic radionuclide-labeled DOTA-GGNle-CycMSH$_{hex}$.

TABLE 1A

DOTA-conjugated lactam bridge-cyclized alpha-MSH peptides.

|  | [a]DOTA-Nle-CycMSH$_{hex}$ | DOTA-GGNle-CycMSH$_{hex}$ | DOTA-GENle-CycMSH$_{hex}$ | DOTA-NleGE-CycMSH$_{hex}$ |
|---|---|---|---|---|
| Amino acid linker between DOTA and the cyclic peptide moiety | -Nle- | -Gly-Gly-Nle- | -Gly-Glu-Nle- | -Nle-Gly-Glu- |
| Calculated molecular weight (Da) | 1368.5 | 1482.6 | 1554.6 | 1554.6 |
| Found molecular weight (Da) | 1368.2 | 1482.0 | 1554.0 | 1554.0 |
| Molecular Formula | $C_{64}H_{93}N_{19}O_{15}$ | $C_{68}H_{99}N_{21}O_{17}$ | $C_{71}H_{103}N_{21}O_{19}$ | $C_{71}H_{103}N_{21}O_{19}$ |
| MC1R binding affinity (nM) | 1.8 | 2.1 | 11.5 | 873.4 |
| HPLC retention time (min) | 14.3 | 14.8 | 15.4 | 9.6 |
| HPLC retention time for $^{111}$In-conjugate (min) | 10.7 | 17.7 | 21.7 | N/A |

[a]The Data of DOTA-Nle-CycMSH$_{hex}$ was cited from Reference 19 for comparison.

TABLE 2A

Biodistribution of $^{111}$In-DOTA-GGNle-CycMSH$_{hex}$ and $^{111}$In-DOTA-GENle-CycMSH$_{hex}$ in B16/F1 melanoma-bearing C57 mice. The data were presented as percent injected dose/gram or as percent injected dose (mean ± SD, n = 5)

|  | $^{111}$In-DOTA-GGNle-CycMSH$_{hex}$ | | | | $^{111}$In-DOTA-GENle-CycMSH$_{hex}$ | | | |
|---|---|---|---|---|---|---|---|---|
| Tissues | 0.5 h | 2 h | 4 h | 24 h | 0.5 h | 2 h | 4 h | 24 h |
| | Percent injected dose/gram (% ID/g) | | | | | | | |
| Tumor | 18.39 ± 2.22 | 19.05 ± 5.04 | 18.6 ± 3.56 | 6.77 ± 0.84 | 11.75 ± 2.00* | 8.99 ± 1.91* | 5.3 ± 2.84* | 4.40 ± 0.87* |
| Brain | 0.21 ± 0.18 | 0.03 ± 0.03 | 0.04 ± 0.03 | 0.01 ± 0.01 | 0.07 ± 0.01 | 0.02 ± 0.01 | 0.04 ± 0.04 | 0.03 ± 0.01 |
| Blood | 3.17 ± 0.45 | 0.12 ± 0.11 | 0.01 ± 0.01 | 0.02 ± 0.01 | 1.28 ± 0.09 | 0.16 ± 0.05 | 0.14 ± 0.06 | 0.01 ± 0.01 |
| Heart | 1.35 ± 0.26 | 0.24 ± 0.12 | 0.01 ± 0.02 | 0.01 ± 0.01 | 0.66 ± 0.17 | 0.06 ± 0.04 | 0.06 ± 0.04 | 0.06 ± 0.02 |
| Lung | 2.97 ± 0.71 | 0.28 ± 0.07 | 0.13 ± 0.10 | 0.07 ± 0.05 | 1.31 ± 0.29 | 0.31 ± 0.14 | 0.20 ± 0.04 | 0.12 ± 0.05 |
| Liver | 1.41 ± 0.22 | 0.57 ± 0.09 | 0.60 ± 0.10 | 0.60 ± 0.10 | 0.67 ± 0.17 | 0.50 ± 0.12 | 0.36 ± 0.03 | 0.26 ± 0.01 |
| Spleen | 0.93 ± 0.37 | 0.17 ± 0.06 | 0.15 ± 0.10 | 0.12 ± 0.13 | 0.54 ± 0.13 | 0.24 ± 0.11 | 0.19 ± 0.10 | 0.14 ± 0.01 |
| Stomach | 2.18 ± 0.28 | 1.30 ± 0.12 | 1.14 ± 0.13 | 1.17 ± 0.48 | 0.95 ± 0.15 | 0.28 ± 0.03 | 0.49 ± 0.14 | 0.41 ± 0.01 |
| Kidneys | 15.19 ± 2.75 | 6.84 ± 0.92 | 6.82 ± 1.19 | 5.44 ± 1.58 | 9.06 ± 2.20* | 5.54 ± 0.63* | 6.25 ± 0.51 | 4.21 ± 0.03 |
| Muscle | 0.37 ± 0.26 | 0.01 ± 0.01 | 0.02 ± 0.02 | 0.02 ± 0.01 | 0.32 ± 0.09 | 0.06 ± 0.03 | 0.11 ± 0.05 | 0.09 ± 0.01 |

TABLE 2A-continued

Biodistribution of $^{111}$In-DOTA-GGNle-CycMSH$_{hex}$ and $^{111}$In-DOTA-GENle-CycMSH$_{hex}$ in B16/F1 melanoma-bearing C57 mice.
The data were presented as percent injected dose/gram or as percent injected dose (mean ± SD, n = 5)

| Tissues | $^{111}$In-DOTA-GGNle-CycMSH$_{hex}$ | | | | $^{111}$In-DOTA-GENle-CycMSH$_{hex}$ | | | |
|---|---|---|---|---|---|---|---|---|
| | 0.5 h | 2 h | 4 h | 24 h | 0.5 h | 2 h | 4 h | 24 h |
| Pancreas | 0.99 ± 0.27 | 0.23 ± 0.12 | 0.14 ± 0.06 | 0.10 ± 0.01 | 0.40 ± 0.08 | 0.12 ± 0.10 | 0.13 ± 0.08 | 0.15 ± 0.04 |
| Bone | 0.59 ± 0.39 | 0.10 ± 0.09 | 0.10 ± 0.08 | 0.04 ± 0.04 | 0.13 ± 0.10 | 0.08 ± 0.05 | 0.02 ± 0.01 | 0.06 ± 0.01 |
| Skin | 2.16 ± 1.28 | 0.27 ± 0.12 | 0.27 ± 0.28 | 0.26 ± 0.08 | 1.63 ± 0.43 | 0.37 ± 0.11 | 0.12 ± 0.10 | 0.16 ± 0.13 |
| Percent injected dose (% ID) | | | | | | | | |
| Intestines | 1.65 ± 0.26 | 1.30 ± 0.32 | 0.97 ± 0.38 | 0.74 ± 0.13 | 0.95 ± 0.14 | 0.68 ± 0.26 | 1.45 ± 0.85 | 0.76 ± 0.45 |
| Urine | 60.80 ± 4.05 | 88.46 ± 1.75 | 88.39 ± 3.06 | 93.23 ± 1.60 | 83.56 ± 0.49 | 89.65 ± 6.24 | 91.38 ± 1.85 | 93.57 ± 0.12 |
| Uptake ratio of tumor/normal tissue | | | | | | | | |
| Tumor/Blood | 5.80 | 158.75 | 1860.00 | 338.50 | 9.18 | 56.19 | 37.86 | 440.00 |
| Tumor/Kidneys | 1.21 | 2.79 | 2.73 | 1.24 | 1.30 | 1.62 | 0.85 | 1.05 |
| Tumor/Lung | 6.19 | 68.04 | 143.08 | 96.71 | 8.97 | 29.00 | 26.50 | 36.67 |
| Tumor/Liver | 13.04 | 33.42 | 31.00 | 11.28 | 17.54 | 17.98 | 14.72 | 16.92 |
| Tumor/Muscle | 49.70 | 1905.00 | 930.00 | 338.50 | 36.72 | 149.83 | 48.18 | 48.89 |
| Tumor/Skin | 8.51 | 70.56 | 68.89 | 26.04 | 7.21 | 24.30 | 44.17 | 27.50 |

$P < 0.05$, significance comparison in tumor and kidney uptakes between $^{111}$In-DOTA-GGNle-CycMSH$_{hex}$ and $^{111}$In-DOTA-GENle-CycMSH$_{hex}$.

Conclusions

The amino acid linkers exhibited profound effects on the melanoma targeting and pharmacokinetic properties of the $^{111}$In-labeled lactam bridge-cyclized α-MSH peptides. Introduction of the -GlyGly- linker maintained high melanoma uptake while reducing the renal and liver uptakes of $^{111}$In-DOTA-GlyGlyNle-CycMSH$_{hex}$, highlighting its potential as an effective imaging probe for melanoma detection, as well as a therapeutic peptide for melanoma treatment when labeled with a therapeutic radionuclide.

The terms and expressions that have been employed in this application are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

REFERENCES (FIRST SET)

1. Jemal A, Siegel R, Ward E, Hao Y, Xu J, Thun M J. Cancer statistics, 2009. *CA Cancer J Clin.* 2009; 59:225-249.
2. Alonso O, Martinez M, Delgado L, et al. Staging of regional lymph nodes in melanoma patients by means of $^{99m}$Tc-MIBI scintigraphy. *J Nucl Med.* 2003; 44:1561-1565.
3. Nabi H A, Zubeldia J M. Clinical application of $^{18}$F-FDG in oncology. *J Nucl Med Technol.* 2002; 30:3-9.
4. Dimitrakopoulou-Strauss A, Strauss L G, Burger C. Quantitative PET studies in pretreated melanoma patients: A comparison of 6-[$^{18}$F]fluoro-L-DOPA with $^{18}$F-FDG and $^{15}$O-water using compartment and non-compartment analysis. *J Nucl Med.* 2001; 42:248-256.
5. Miao Y, Whitener D, Feng W, Owen N K, Chen J, Quinn T P. Evaluation of the human melanoma targeting properties of radiolabeled alpha-melanocyte stimulating hormone peptide analogues. *Bioconjug Chem.* 2003; 14:1177-1184.
6. Miao Y, Owen N K, Whitener D, Gallazzi F, Hoffman T J, Quinn T P. In vivo evaluation of $^{188}$Re-labeled alpha-melanocyte stimulating hormone peptide analogs for melanoma therapy. *Int J Cancer.* 2002; 101:480-487.
7. Chen J, Cheng Z, Hoffman T J, Jurisson S S, Quinn T P. Melanoma-targeting properties of $^{99m}$technetium-labeled cyclic alpha-melanocyte-stimulating hormone peptide analogues. *Cancer Res.* 2000; 60:5649-5658.
8. Siegrist W, Solca F, Stutz S, et al. Characterization of receptors for alpha-melanocyte-stimulating hormone on human melanoma cells. *Cancer Res.* 1989; 49:6352-6358.
9. Tatro J B, Reichlin S. Specific receptors for alpha-melanocyte-stimulating hormone are widely distributed in tissues of rodents. *Endocrinology* 1987; 121:1900-1907.
10. Miao Y, Owen N K, Fisher D R, Hoffman T J, Quinn T P. Therapeutic efficacy of a $^{188}$Re-labeled alpha-melanocyte-stimulating hormone peptide analog in murine and human melanoma-bearing mouse models. *J Nucl Med.* 2005; 46:121-129.
11. Miao Y, Hylarides M, Fisher D R, et al. Melanoma therapy via peptide-targeted alpha-radiation. *Clin Cancer Res.* 2005; 11:5616-5621.
12. Froidevaux S, Calame-Christe M, Tanner H, Eberle A N. Melanoma targeting with DOTA-alpha-melanocyte-stimulating hormone analogs: structural parameters affecting tumor uptake and kidney uptake. *J Nucl Med.* 2005; 46:887-895.
13. Froidevaux S, Calame-Christe M, Schuhmacher J, et al. A gallium-labeled DOTA-alpha-melanocyte-stimulating hormone analog for PET imaging of melanoma metastases. *J Nucl Med.* 2004; 45:116-123.

14. Froidevaux S, Calame-Christe M, Tanner H, Sumanovski L, Eberle A N. A novel DOTA-alpha-melanocyte-stimulating hormone analog for metastatic melanoma diagnosis. *J Nucl Med.* 2002; 43:1699-1706.
15. Wei L, Butcher C, Miao Y, et al. Synthesis and biologic evaluation of $^{64}$Cu-labeled rhenium-cyclized alpha-MSH peptide analog using a cross-bridged cyclam chelator. *J Nucl Med.* 2007; 48:64-72.
16. Miao Y, Benwell K, Quinn T P. $^{99m}$Tc- and $^{111}$In-labeled alpha-melanocyte-stimulating hormone peptides as imaging probes for primary and pulmonary metastatic melanoma detection. *J Nucl Med.* 2007; 48:73-80.
17. Cheng Z, Chen J, Miao Y, Owen N K, Quinn T P, Jurisson S S. Modification of the structure of a metallopeptide: synthesis and biological evaluation of $^{111}$In-labeled DOTA-conjugated rhenium-cyclized alpha-MSH analogues. *J Med Chem.* 2002; 45:3048-3056.
18. Cheng Z, Xiong Z, Subbarayan M, Chen X, Gambhir S S. $^{64}$Cu-labeled alpha-melanocyte-stimulating hormone analog for MicroPET imaging of melanocortin 1 receptor expression. *Bioconjug Chem.* 2007; 18:765-772.
19. Miao Y, Gallazzi F, Guo H, Quinn T P. $^{111}$In-labeled lactam bridge-cyclized alpha-melanocyte stimulating hormone peptide analogues for melanoma imaging. *Bioconjug Chem.* 2008; 19:539-547.
20. Guo H, Shenoy N, Gershman B M, Yang J, Sklar L A, Miao Y. Metastatic melanoma imaging with an $^{111}$In-labeled lactam bridge-cyclized alpha-melanocyte-stimulating hormone peptide. *Nucl Med Biol.* 2009; 36:267-276.
21. Sawyer T K, Hruby V J, Darman P S, Hadley M E. [half-Cys$^4$,half-Cys$^{10}$]-α-melanocyte-stimulating hormone: a cyclic α-melanotropin exhibiting superagonist biological activity. *Proc Natl Acad Sci USA.* 1982; 79:1751-1755.
22. Al-Obeidi F, Hadley M E, Pettitt B M, Hruby V J. Design of a new class of superpotent cyclic α-melanotropins based on quenched dynamic simulations. *J Am Chem Soc.* 1989;111:3413-3416.
23. Al-Obeidi F, de L Castrucci A M, Hadley M E, Hruby V J. Potent and prolonged-acting cyclic lactam analogs of α-melanotropin: design based on molecular dynamics. *J Med Chem.* 1989: 32:2555-2561.
24. Fung S, Hruby V J. Design of cyclic and other templates for potent and selective peptide α-MSH analogues. *Curr Opin Chem Biol.* 2005:9:352-358
25. Haskell-Luevano C, Miwa H, Dickinson C, et al. Characterizations of the unusual dissociation properties of melanotropin peptides from the melanocortin receptor, hMC1R. *J Med Chem.* 1996; 39:432-435.
26. Haskell-Luevano C, Toth K, Boteju L, et al. Beta-Methylation of the Phe$^2$ and Trp$^9$ melanotropin side chain pharmacophores affects ligand-receptor interactions and prolonged biological activity. *J Med Chem.* 1997; 40:2740-2749.
27. Chen J, Cheng Z, Owen N K, et al. Evaluation of an $^{111}$In-DOTA-rhenium cyclized alpha-MSH analog: a novel cyclic-peptide analog with improved tumor-targeting properties. *J Nucl Med.* 2001; 42:1847-1855.
28. Raposinho P D, Xavier C, Correia J D, Falcao S, Gomes P, Santos I. Melanoma targeting with alpha-melanocyte stimulating hormone analogs labeled with fac-[$^{99m}$Tc(CO)$_3$]$^+$: effect of cyclization on tumor-seeking properties. *J Biol Inorg Chem.* 2008; 13:449-459.
29. Raposinho P D, Correia J D, Alves S, Botelho M F, Santos A C, and Santos I. A $^{99m}$Tc(CO)$_3$-labeled pyrazolyla-melanocyte-stimulating hormone analog conjugate for melanoma targeting. *Nucl Med Biol.* 2008; 35:91-99.

REFERENCES (SECOND SET FOR FURTHER EXAMPLES SECTION)

1. Siegrist W, Solca F, Stutz S, et al. Characterization of receptors for alpha-melanocyte-stimulating hormone on human melanoma cells. Cancer Res 1989; 49:6352-8.
2. Tatro J B, Reichlin S. Specific receptors for alpha-melanocyte-stimulating hormone are widely distributed in tissues of rodents. Endocrinology 1987; 121:1900-7.
3. Miao Y, Whitener D, Feng W, Owen N K, Chen J, Quinn T P. Evaluation of the human melanoma targeting properties of radiolabeled alpha-melanocyte stimulating hormone peptide analogues. Bioconjug Chem 2003; 14:1177-84.
4. Miao Y, Owen N K, Whitener D, Gallazzi F, Hoffman T J, Quinn T P. In vivo evaluation of $^{188}$Re-labeled alpha-melanocyte stimulating hormone peptide analogs for melanoma therapy. Int J Cancer 2002; 101:480-7.
5. Chen J, Cheng Z, Hoffman T J, Jurisson S S, Quinn T P. Melanoma-targeting properties of $^{99m}$technetium-labeled cyclic alpha-melanocyte-stimulating hormone peptide analogues. Cancer Res 2000; 60:5649-58.
6. Froidevaux S, Calame-Christe M, Tanner H, Eberle A N. Melanoma targeting with DOTA-alpha-melanocyte-stimulating hormone analogs: structural parameters affecting tumor uptake and kidney uptake. J Nucl Med 2005; 46:887-95.
7. Froidevaux S, Calame-Christe M, Schuhmacher J, et al. A gallium-labeled DOTA-alpha-melanocyte-stimulating hormone analog for PET imaging of melanoma metastases. J Nucl Med 2004; 45:116-23.
8. Froidevaux S, Calame-Christe M, Tanner H, Sumanovski L, Eberle A N. A novel DOTA-alpha-melanocyte-stimulating hormone analog for metastatic melanoma diagnosis. J Nucl Med 2002; 43:1699-706.
9. Miao Y, Owen N K, Fisher D R, Hoffman T J, Quinn T P. Therapeutic efficacy of a $^{188}$Re-labeled alpha-melanocyte-stimulating hormone peptide analog in murine and human melanoma-bearing mouse models. J Nucl Med 2005; 46:121-9.
10. Miao Y, Hylarides M, Fisher D R, et al. Melanoma therapy via peptide-targeted alpha-radiation. Clin Cancer Res 2005; 11:5616-21.
11. Wei L, Butcher C, Miao Y, et al. Synthesis and biologic evaluation of $^{64}$Cu-labeled rhenium-cyclized alpha-MSH peptide analog using a cross-bridged cyclam chelator. J Nucl Med 2007; 48:64-72.
12. Miao Y, Benwell K, Quinn T P. $^{99m}$Tc- and $^{111}$In-labeled alpha-melanocyte-stimulating hormone peptides as imaging probes for primary and pulmonary metastatic melanoma detection. J Nucl Med 2007; 48:73-80.
13. Cheng Z, Chen J, Miao Y, Owen N K, Quinn T P, Jurisson S S. Modification of the structure of a metallopeptide: synthesis and biological evaluation of $^{111}$In-labeled DOTA-conjugated rhenium-cyclized alpha-MSH analogues. J Med Chem 2002; 45:3048-56.
14. Cheng Z, Xiong Z, Subbarayan M, Chen X, Gambhir S S. $^{64}$Cu-labeled alpha-melanocyte-stimulating hormone analog for MicroPET imaging of melanocortin 1 receptor expression. Bioconjug Chem 2007; 18:765-72.
15. Miao Y, Gallazzi F, Guo H, Quinn T P. $^{111}$In-labeled lactam bridge-cyclized alpha-melanocyte stimulating hormone peptide analogues for melanoma imaging. Bioconjug Chem 2008; 19:539-47.

16. Guo H, Shenoy N, Gershman B M, Yang J, Sklar L A, Miao Y. Metastatic melanoma imaging with an $^{111}$In-labeled lactam bridge-cyclized alpha-melanocyte-stimulating hormone peptide. Nucl Med Biol 2009; 36:267-76.
17. Guo H, Yang J, Gallazzi F, Prossnitz E R, Sklar L A, Miao Y. Effect of DOTA position on melanoma targeting and pharmacokinetic properties of $^{111}$In-labeled lactam bridge-cyclized α-melanocyte stimulating hormone peptide. Bioconjug Chem 2009; 20:2162-68.
18. Guo H, Yang J, Shenoy N, Miao Y. Gallium-67-labeled lactam bridge-cyclized alpha-melanocyte stimulating hormone peptide for primary and metastatic melanoma imaging. Bioconjug Chem 2009; 20:2356-63.
19. Guo H, Yang J, Gallazzi F, Miao Y. Reduction of the ring size of radiolabeled lactam bridge-cyclized alpha-MSH peptide resulting in enhanced melanoma uptake. J Nucl Med 2010; 51:418-26.
20. Chen J, Cheng Z, Owen N K, Hoffman T J, Miao Y, Jurisson S S, Quinn T P. Evaluation of an $^{111}$In-DOTA-rhenium cyclized α-MSH analog: a novel cyclic-peptide analog with improved tumor-targeting properties. J Nucl Med 2001; 42:1847-55.
21. Hoffman T J, Gali H, Smith C J, Sieckman G L, Hayes D L, Owen N K, Volkert W A. Novel series of $^{111}$In-labeled bombesin analogs as potential radiopharmaceuticals for specific targeting of gastrin-releasing peptide receptors expressed on human prostate cancer cells. J Nucl Med 2003; 44:823-31.
22. Garayoa E G, Schweinsberg C, Maes V, Brans L, Blauenstein P, Tourwe D A, Schibli R, Schbiger P A. Influence of the molecular charge on the biodistribution of bombesin analogues labeled with the [$^{99m}$Tc(CO)$_3$]-core. Bioconjug Chem 2008; 19:2409-16.
23. Fragogeorgi E A, Zikos C, Gourni E, Bouziotis P, Paravatou-Petsotas M, Loudos G, Mitsokapas N, Xanthopoulos S, Mavri-Vavayanni M, Livaniou E, Varvarigou A D, Archimandritis S C. Spacer site modifications for the improvement of the in vitro and in vivo binding properties of $^{99m}$Tc-N$_3$S—X-Bombesin[2-14] derivatives. Bioconjug Chem 2009; 20: 856-67.
24. Garrison J C, Rold T L, Sieckman G L, Naz F, Sublett S V, Figueroa S D, Volkert W A, Hoffman T J: Evaluation of the pharmacokinetic effects of various linking group using the $^{111}$In-DOTA-X-BBN(7-14)NH$_2$ structural paradigm in a prostate cancer model. Bioconjug Chem 2008; 19: 1803-12.
25. Parry J J, Kelly T S, Andrews R, Rogers B E. In vitro and in vivo evaluation of $^{64}$Cu-labeled DOTA-Linker-Bombesin(7-14) analogues containing different amino acid linker moieties. Bioconjug Chem 2007; 18:1110-7.
26. Liu S, He Z, Hsieh W Y, Kim Y S, Jiang Y. Impact of PKM linkers on biodistribution characteristics of the $^{99m}$Tc-labeled cyclic RGDfK dimer. Bioconjug Chem 2006; 17:1499-507.
27. Shi J, Wang L, Kim Y S, Zhai S, Liu Z, Chen X, Liu S. Improving tumor uptake and excretion kinetics of $^{99m}$Tc-labeled cyclic arginine-glycine-aspartic (RGD) dimers with triglycine linkers. J Med Chem 2008; 51:7980-90.
28. Wang L, Shi J, Kim Y S, Zhai S, Jia B, Zhao H, Liu Z, Wang F, Chen X, Liu S. Improving tumor-targeting capability and pharmacokinetics of $^{99m}$Tc-labeled cyclic RGD dimers with PEG$_4$ linkers. Mol Pharm 2009; 6:231-45.
29. Shi J, Kim Y S, Zhai S, Liu Z, Chen X, Liu S. Improving tumor uptake and pharmacokinetics of $^{64}$Cu-labeled cyclic RGD peptide dimers with Gly$_3$ and PEG$_4$ linkers. Bioconjug Chem 2009; 20:750-9.

The invention claimed is:

1. A method of treating melanoma in a patient in need thereof comprising administering to said patient an effective amount of a compound according to the chemical structure:

$(Y^1)$—X-(ABC)-CycMSH$_{hex}$ where $Y^1$ is a 1,4,7,10-tetraazacyclododecane-1,4,7,10-tetraacetic acid (DOTA), 1,4,7-triazacyclononane-1,4,7-triacetic acid (NOTA) or hydrazinonicotinamide (HYNIC) group, wherein $Y^1$ incorporates or complexes with a radioisotope selected from the group consisting of $^{86}$Y, $^{111}$In, $^{225}$Ac, $^{212}$Bi, $^{213}$Bi, $^{71}$As, $^{72}$As, $^{76}$As, $^{77}$As, $^{65}$Zn, $^{48}$V, $^{203}$Pb, $^{209}$Pb, $^{212}$Pb, $^{166}$Ho, $^{149}$Pm, $^{153}$Sm, $^{67}$Ga, $^{68}$Ga, $^{64}$Cu, $^{67}$Cu, $^{188}$Re, $^{186}$Re and $^{99m}$Tc;

X is absent or is a

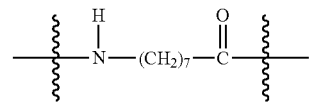

group;

ABC is GGNle when X is absent or is Nle when X is a

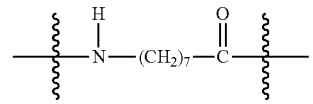

group;

CycMSH$_{hex}$ is a cyclic peptide comprising six amino acids according to the general structure:

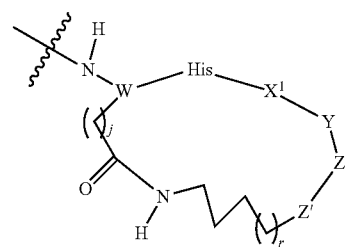

wherein W is a C—H group from an aspartic acid or glutamic acid residue, wherein the alkylene carboxylic acid sidechain of said aspartic acid or glutamic acid and the alkyleneamine sidechain of lysine or ornithine are bonded together to form an amide linkage as indicated;
$X^1$ is D-phenylalanine;
Y is arginine;
Z is tryptophan;
Z' and the alkyleneamine to which Z' is attached is Lys(CONH$_2$) or Orn(CONH$_2$);
j is 1 or 2; and
r is 0 or 1; or
a pharmaceutically acceptable salt thereof.

2. The method according to claim 1, wherein $Y^1$ is a DOTA group and said compound is complexed with a radioisotope selected from the group consisting of $^{86}$Y, $^{111}$In, $^{225}$Ac, $^{212}$Bi, $^{213}$Bi, $^{71}$As, $^{72}$As, $^{76}$As, $^{77}$As, $^{65}$Zn, $^{48}$V, $^{203}$Pb, $^{209}$Pb, $^{212}$Pb, $^{166}$Ho, $^{149}$Pm and $^{153}$Sm.

3. The method according to claim 1, wherein $Y^1$ is a NOTA group and said compound is complexed with a radioisotope selected from the group consisting of $^{67}$Ga, $^{68}$Ga, $^{64}$Cu, and $^{67}$Cu.

4. The method according to claim 1, wherein $Y^1$ is a HYNIC group and said compound is complexed with a radioisotope which is $^{188}$Re, $^{186}$Re and $^{99m}$Tc.

5. The method according to claim 1, wherein j is 1 and r is 0.

6. The method according to claim 1 wherein j is 2 and r is 1.

7. The method according to claim 1 wherein j is 2 and r is 0.

8. The method according to claim 2 wherein j is 1 and r is 0.

9. The method according to claim 2 wherein j is 2 and r is 1.

10. The method according to claim 2 wherein j is 2 and r is 0.

11. The method according to claim 3 wherein j is 1 and r is 0.

12. The method according to claim 3 wherein j is 2 and r is 1.

13. The method according to claim 3 wherein j is 2 and r is 0.

14. The method according to claim 3 wherein j is 1 and r is 0.

15. The method according to claim 4 wherein j is 2 and r is 1.

16. The method according to claim 4 wherein j is 2 and r is 0.

17. The method according to claim 1 wherein X is absent and ABC is a GGNle group.

18. The method according to claim 1 wherein X is

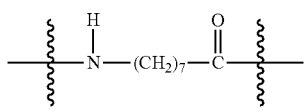

and ABC is a Nle group.

19. The method according to claim 1 wherein said compound is co-administered in combination with an effective amount of dacarbazine (DTIC), interleukin-2 (IL-2), alpha-interferon and mixtures thereof.

20. A method of diagnosing the existence, absence or extent of melanoma in a patient comprising administering to said patient an imaging effective amount of a compound according to the chemical structure:

where $Y^1$ is a 1,4,7,10-tetraazacyclododecane-1,4,7,10-tetraacetic acid (DOTA), 1,4,7-triazacyclononane-1,4,7-triacetic acid (NOTA) or hydrazinonicotinamide (HYNIC) group, wherein $Y^1$ incorporates or complexes with a radioisotope selected from the group consisting of $^{86}$Y, $^{111}$In, $^{225}$Ac, $^{212}$Bi, $^{213}$Bi, $^{71}$As, $^{72}$As, $^{76}$As, $^{77}$As, $^{65}$Zn, $^{48}$V, $^{203}$Pb, $^{209}$Pb, $^{212}$Pb, $^{166}$Ho, $^{149}$Pm, $^{153}$Sm, $^{67}$Ga, $^{68}$Ga, $^{64}$Cu, $^{67}$Cu, $^{188}$Re, $^{186}$Re and $^{99m}$Tc;

X is absent or is a

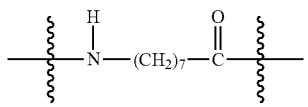

group;

ABC is GGNle when X is absent or is Nle when X is a

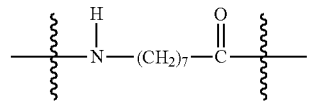

group;

CycMSH$_{hex}$ is a cyclic peptide comprising six amino acids according to the general structure:

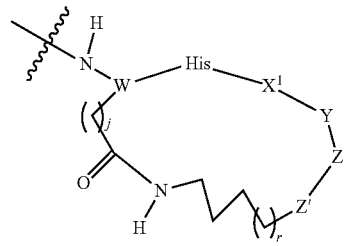

wherein W is a C—H group from an aspartic acid or glutamic acid residue, wherein the alkylene carboxylic acid sidechain of said aspartic acid or glutamic acid and the alkyleneamine sidechain of lysine or ornithine are bonded together to form an amide linkage as indicated;
$X^1$ is D-phenylalanine;
Y is arginine;
Z is tryptophan;
Z' and the alkyleneamine to which Z' is attached is Lys(CONH$_2$) or Orn(CONH$_2$);
j is 1 or 2; and
r is 0 or 1; or
a pharmaceutically acceptable salt thereof;
imaging said patient to determine if tissue in said patient exhibits elevated expression of MSH receptors; and
diagnosing said patient as having melanoma if said tissue evidences elevated expression of MSH receptors in comparison to a standard.

21. The method according to claim 20, wherein j is 1 or 2 and r is 0 or 1.

22. The method according to claim 20 wherein j is 1 or 2 and r is 1.

23. The method according to claim 20 wherein j is 1 or 2 and r is 0.

24. The method according to claim 20 wherein j is 1 and r is 0 or 1.

25. The method according to claim 20 wherein j is 2 and r is 0 or 1.

26. The method according to claim 20 wherein X is absent and ABC is a GGNle group.

27. The method according to claim 20 wherein X is

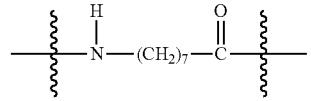

and ABC is a Nle group.

28. A method of monitoring therapy of a patient in the treatment of melanoma, the method comprising administering to a patient undergoing melanoma treatment an imaging effective amount of a compound according to the chemical structure:

where $Y^1$ is a 1,4,7,10-tetraazacyclododecane-1,4,7,10-tetraacetic acid (DOTA), 1,4,7-triazacyclononane-1,4,7-triacetic acid (NOTA) or hydrazinonicotinamide (HYNIC) group, wherein $Y^1$ incorporates or complexes with a radioisotope selected from the group consisting of $^{86}Y$, $^{111}In$, $^{225}Ac$, $^{212}Bi$, $^{213}Bi$, $^{71}As$, $^{72}As$, $^{76}As$, $^{77}As$, $^{65}Zn$, $^{48}V$, $^{203}Pb$, $^{209}Pb$, $^{212}Pb$, $^{166}Ho$, $^{149}Pm$, $^{153}Sm$, $^{67}Ga$, $^{68}Ga$, $^{64}Cu$, $^{67}Cu$, $^{188}Re$, $^{186}Re$ and $^{99m}Tc$;

X is absent or is a

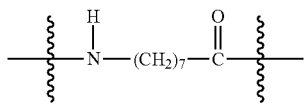

group;

ABC is GGNle when X is absent or is Nle when X is a

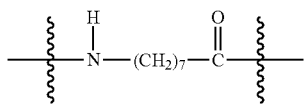

group;

CycMSH$_{hex}$ is a cyclic peptide comprising six amino acids according to the general structure:

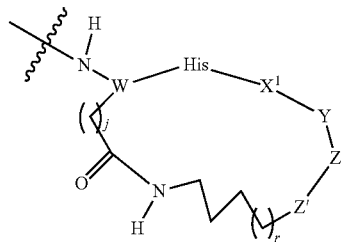

wherein W is a C—H group from an aspartic acid or glutamic acid residue, wherein the alkylene carboxylic acid sidechain of said aspartic acid or glutamic acid and the alkyleneamine sidechain of lysine or ornithine are bonded together to form an amide linkage as indicated;

$X^1$ is D-phenylalanine;

Y is arginine;

Z is tryptophan;

Z' and the alkyleneamine to which Z' is attached is Lys(CONH$_2$) or Orn(CONH$_2$);

j is 1 or 2; and r is 0 or 1; or a pharmaceutically acceptable salt thereof;

imaging said patient to determine if tissue in said patient exhibits elevated expression of MSH receptors and comparing the results of said imaging with a standard.

29. The method according to claim 28 wherein the therapy of said patient is continued, modified or terminated based upon a comparison of said elevated expression of MSH receptors with said standard.

* * * * *